United States Patent

Suzuki et al.

[11] Patent Number: 5,348,847
[45] Date of Patent: * Sep. 20, 1994

[54] SILVER HALIDE COLOR PHOTOGRAPHIC MATERIAL

[75] Inventors: Makoto Suzuki; Osamu Takahashi; Yasuhiro Shimada; Koushin Matsuoka; Yasuhiro Yoshioka, all of Kanagawa, Japan

[73] Assignee: Fuji Photo Film Co., Ltd., Kanagawa, Japan

[*] Notice: The portion of the term of this patent subsequent to Oct. 26, 2010 has been disclaimed.

[21] Appl. No.: 982,445

[22] Filed: Nov. 27, 1992

[30] Foreign Application Priority Data

Nov. 27, 1991 [JP] Japan .................. 3-311212
Nov. 27, 1991 [JP] Japan .................. 3-335861
Feb. 21, 1992 [JP] Japan .................. 4-70002

[51] Int. Cl.$^5$ .................................... G03C 7/38
[52] U.S. Cl. .................................... 430/558; 430/384; 430/385
[58] Field of Search .................. 430/558, 384, 385

[56] References Cited

U.S. PATENT DOCUMENTS

| 4,093,728 | 6/1978 | Wade et al. | 548/262.4 |
| 4,728,598 | 3/1988 | Bailey et al. | 430/387 |
| 4,910,127 | 3/1990 | Sakaki et al. | 430/558 |
| 5,256,526 | 10/1993 | Suzuki et al. | 430/558 |

FOREIGN PATENT DOCUMENTS

| 0249453 | 12/1987 | European Pat. Off. . |
| 0252288 | 1/1988 | European Pat. Off. . |
| 0456226 | 11/1991 | European Pat. Off. . |
| 0491197 | 6/1992 | European Pat. Off. ........ 430/558 |

Primary Examiner—Lee C. Wright
Attorney, Agent, or Firm—Sughrue, Mion, Zinn, Macpeak & Seas

[57] ABSTRACT

Disclosed is a silver halide color photographic material comprising a support having thereon at least one layer containing one or more cyan couplers of formula (I):

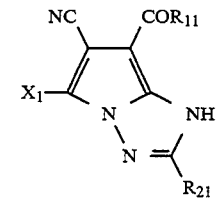

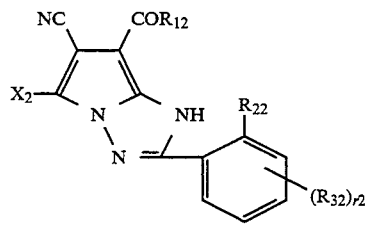

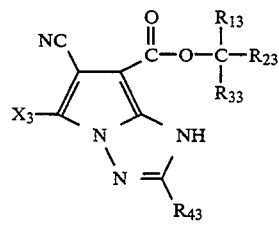

wherein $R_{11}$ represents a branched or cyclic alkyl group, a branched or cyclic alkoxy group, a substituted aryl group, or a substituted aryloxy group; $R_{21}$ represents a substituent which may optionally be substituted. $R_{12}$ represents an aliphatic group, an aryl group, a heterocyclic group, an alkoxy group, an aryloxy group, an alkylamino group, an anilino group, a heterocyclic-oxy group, or a heterocyclic-amino group; $R_{22}$ and $R_{32}$ each represents a substituent; $r_2$ represents an integer of from 0 to 4; provided that when $r_2$ is a plural number, the plurality of $R_{32}$ groups may be the same or different; $R_{13}$, $R_{23}$ and $R_{33}$ each represent a hydrogen atom or a substituent; provided that the total of Taft's substituent constant $\sigma^*$ values of $R_{13}$, $R_{23}$ and $R_{33}$ is 1.5 or more; $R_{43}$ represents a substituent. In formulae (I), (II) and (III), $X_1$, $X_2$ and $X_3$ each represents a hydrogen atom, or a group which is capable of splitting off from the formula by a coupling reaction with an oxidation product (Abstract continued on next page.)

of an aromatic primary amine color developing agent; and the group of $R_{11}$, $R_{21}$ or $X_1$, the group of $R_{12}$, $R_{22}$, $R_{32}$ or $X_2$, or the group of $R_{13}$, $R_{23}$, $R_{33}$, $R_{43}$ or $X_3$ may be a divalent group to form a dimer or a higher polymer or to bond to a polymer chain to form a homopolymer or a copolymer. The material forms a color image with good color hue and color fastness. It is hardly fogged, and the dyes formed from the couplers hardly associate with each other in the material.

18 Claims, No Drawings

SILVER HALIDE COLOR PHOTOGRAPHIC MATERIAL

FIELD OF THE INVENTION

The present invention relates to a silver halide color photographic material.

BACKGROUND OF THE INVENTION

It is well known to form a color image by reacting an oxidized aromatic primary amine color developing agent and a coupler with an exposed silver halide as an oxidizing agent to give an indophenol, indoaniline, indamine, azomethine, phenoxazine, phenazine or the like dye. In such a photographic system, subtractive color photography is used, and color images are formed of yellow, magenta and cyan dyes.

For producing cyan color images, phenol or naphthol couplers are generally used. However, since these couplers have an unfavorable absorption in the green range, they have a serious problem in that they noticeably lower color reproducibility. Therefore, there is a need to overcome this problem.

As a means for overcoming the problem, the heterocyclic compounds described in U.S. Pat. Nos. 4,728,598 and 4,873,185 and European Patent 249,453A2 have been proposed. However, these have severe problems in that the coupling activity thereof is low and the dyes formed therefrom have poor fastness to heat and light. As couplers free from these problems, the pyrrolopyrazoles described in European Patent Laid-Open No. 0456226 have been proposed. These couplers are excellent with respect to coupling activity, color hue and fastness of the dyes formed therefrom, and therefore they may be fairly improved heterocyclic cyan couplers. However, they still are insufficient for practical use. In particular, they have problems in that the dyes formed therefrom often associate with each other in oil droplets to give unnecessary absorption peaks and the cyan fog in the non-exposed area immediately after development is great.

SUMMARY OF THE INVENTION

Therefore, one object of the present invention is to provide a silver halide color photographic material containing a cyan coupler(s) having a high coupling activity and being able to form a dye having an excellent color hue and a high color fastness.

Another object of the present invention is to provide a silver halide color photographic material containing a cyan coupler(s) capable of forming a low associating dye.

A further object of the present invention is to provide a silver halide color photographic material containing a cyan coupler(s) which causes little color fog in the non-exposed area of the material.

These and other objects of the present invention have been attained by a silver halide color photographic material containing at least one cyan coupler of the following general formulae (I), (II) and (III) in at least one layer on a support:

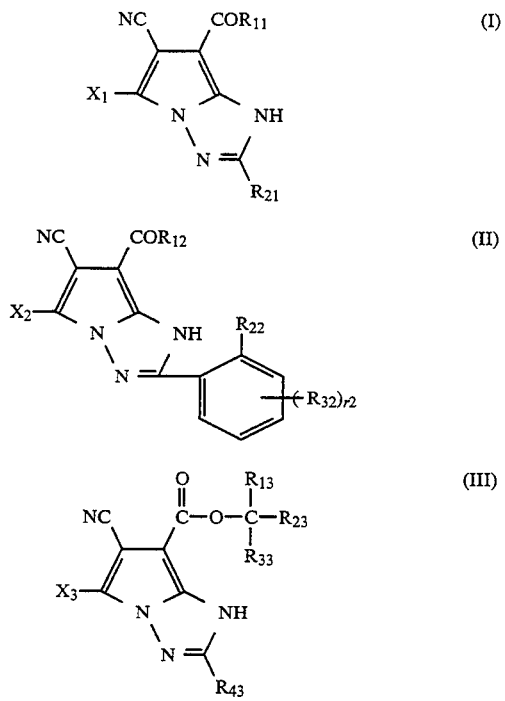

wherein $R_{11}$ represents a branched or cyclic alkyl group, a branched or cyclic alkoxy group, a substituted aryl group, or a substituted aryloxy group, $R_{21}$ represents a substituent;

$R_{12}$ represents an aliphatic group, an aryl group, a heterocyclic group, an alkoxy group, an aryloxy group, an alkylamino group, an arylamino group, a heterocyclic-oxy group or a heterocyclic-amino group;

$R_{22}$ and $R_{32}$ each represents a substituent;

$r_2$ represents an integer of from 0 to 4; provided that when $r_2$ is a plural number, the plurality of $R_{32}$ groups may be the same or different;

$R_{13}$, $R_{23}$ and $R_{33}$ each represents a hydrogen atom or a substituent; provided that the total of Taft's substituent constant $\sigma^*$ values of $R_{13}$, $R_{23}$ and $R_{33}$ is 1.5 or more;

$R_{43}$ represents a substituent;

$X_1$, $X_2$ and $X_3$ each represents a hydrogen atom or a group which is capable of splitting off from the formula by a coupling reaction with an oxidation product of an aromatic primary amine color developing agent; and a group represented by $R_{11}$, $R_{21}$ or $X_1$, a group represented by $R_{12}$, $R_{22}$, $R_{32}$ or $X_2$, or a group $R_{13}$, $R_{23}$, $R_{33}$, $R_{43}$ or $X_3$ may be divalent and form a dimer or a higher polymer or bond to a polymer chain to form a homopolymer or a copolymer.

DETAILED DESCRIPTION OF THE INVENTION

Compounds of the present invention are described in detail hereunder.

In formula (I), $R_{11}$ represents a branched or cyclic alkyl group preferably having from 3 to 30 carbon atoms, a branched or cyclic alkoxy group preferably having from 3 to 30 carbon atoms, or a substituted aryl or aryloxy group preferably having from 6 to 30 carbon atoms. Terms of "branched alkyl group" and "branched alkoxy group" used in the present invention mean the alkyl and alkoxy groups having branched groups in hydrocarbon chain. A branched position in the chain preferably within a fifth carbon atoms, preferably within fourth, more preferably third carbon atoms from the carbon atom connected to CO group.

The branched or cyclic alkyl group, branched or cyclic alkoxy group, substituted aryl group or substituted aryloxy group of $R_{11}$ may be either unsubstituted substituted. The substituents for these groups include those substituents which will be mentioned below as being represented by $R_{31}$ or $R_{41}$. Where $R_{11}$ is a branched alkoxy group, it may be the same branched alkoxy group as in formula (III). Number of carbon atoms for each groups defined in the present specification shows in total number, which includes carbon atoms of substituents if it is further substituted.

Where $R_{11}$ is a branched or cyclic alkyl group, typical examples thereof include an isopropyl group, an isobutyl group, a tert-octyl group, a 2-ethylhexyl group, a 2-hexadecenyl group, a 7-ethyl-2-methyl-4-undecanoyl group, a 3,5,5-trimethyl-1-hexanoyl group and a 2-methylcyclohexyl group.

Where $R_{11}$ is a branched or cyclic alkoxy group, typical examples thereof include an isobutoxy group, a 2-ethylhexyloxy group, a 2-hexadecenyloxy group, a 7-ethyl-2-methyl-4-undecanoyloxy group and a 2-methylcyclohexyloxy group.

Where $R_{11}$ is a substituted aryl group substituted aryloxy group which is preferably represented by the following general formula (IV) or (V), respectively:

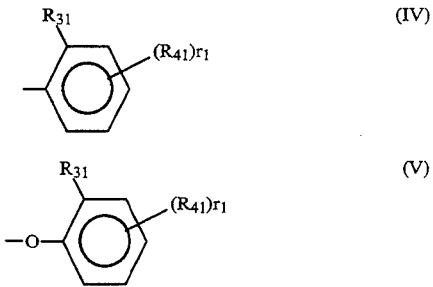

Accordingly, the moiety —$COR_{11}$ may be represented by formulae (IV') or (V'):

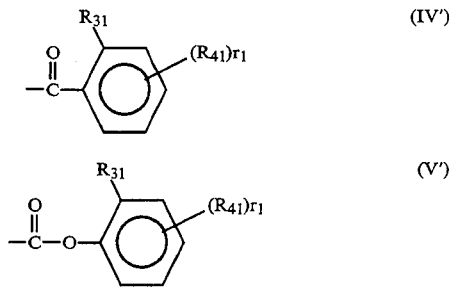

wherein $R_{31}$ and $R_{41}$ may be the same or different and each represents a substituent; and $r_1$ represents an integer of from 0 to 4, and when $r_1$ is a plural number, the plurality of $R_{41}$ groups may be the same or different.

The substituents represented by $R_{31}$ or $R_{41}$ include, for example, a halogen atom (e.g., chlorine, bromine), an aliphatic group (e.g., linear or branched alkyl, aralkyl, alkenyl, alkynyl, cycloalkyl or cycloalkenyl group having from 1 to 70, preferably from 1 to 50, and more preferably 1 to 36 total carbon atoms, precisely, methyl, ethyl, propyl, isopropyl, t-butyl, tridecyl, 2-methanesulfonylethyl, 3-(3-pentadecylphenoxy)propyl, 3-{4-{2-[4-(4-hydroxyphenylsulfonyl)phenoxy]dodecanamido} phenyl}propyl, 2-ethoxytridecyl, trifluoromethyl, cyclopentyl, 3-(2,4-di-t-amylphenoxy)propyl), an aryl group (preferably having from 6 to 76, more preferably from 6 to 56 and especially preferably from 6 to 36 total carbon atoms, e.g., phenyl, naphthyl, 4-hexadecoxyphenyl, 4-t-butylphenyl, 2,4-di-t-amylphenyl, 4-tetradecanamidophenyl , 3-(2,4-tert-amylphenoxyacetamido)phenyl), a heterocyclic group 5- to 9-membered heterocyclic ring containing at least one of hetero atoms, such as a nitrogen, oxygen and sulfur atoms (preferably 5- to 6-membered ring containing a nitrogen atom, as a hetero atom) having from 1 to 70, preferably 2 to 50 total carbon atoms (e.g., 3-pyridyl, 2-furyl, 2-thienyl, 2-pyridyl, 2-pyrimidyl, 2-benzothiazolyl), an alkoxy group having preferably from 1 to 70, more preferably from 1 to 36 total carbon atoms (e.g., methoxy, ethoxy, 2-methoxyethoxy, 2-dodecyloxyethoxy, 2-methanesulfonylethoxy), an aryloxy group having preferably from 6 to 70, more preferably from 6 to 56 total carbon atoms (e.g., phenoxy, 2-methylphenoxy, 4-tert-butylphenoxy, 2,4-di-tert-amylphenoxy, 2-chlorophenoxy, 4-cyanophenoxy, 3-nitrophenoxy, 3-t-butyloxycarbamoylphenoxy, 3-methoxycarbamoylphenoxy), a heterocyclic-oxy group, preferably 5- to 9-membered heterocyclic-oxy group containing at least one of hetero atoms, such as a nitrogen, oxygen and sulfur atoms (more preferably 5- to 6-membered heterocyclic-oxy group) having from 1 to 70, preferably from 2 to 50 total carbon atoms (e.g., 2-benzimidazolytoxy, 1-phenyltetrazolyl-5-oxy, 2-tetrahydropyranyloxy), an alkyl-, aryl- or heterocyclic-thio group having from 1 to 70, preferably 1 to 50 total carbon atoms (e.g., methylthio, ethylthio, octylthio, tetradecylthio, 2-phenoxyethylthio, 3-phenoxypropylthio, 3-(4-tert-butylphenoxy)propylthio, phenylthio, 2-butoxy-5-tert-octylphenylthio, 3-pentadecylphenylthio, 2-carboxyphenylthio, 4-tetradecanamidophenylthio, 2-benzothiazolylthio, 2,4-di-phenoxy-1,3,4-triazol-6-thio, 2-pyridylthio), an acyloxy group having preferably from 2 to 70, more preferably from 2 to 50 total carbon atoms (e.g., acetoxy, hexadecanoyloxy), a carbamoyloxy group having preferably from 1 to 70 , more preferably from 2 to 50 total carbon atoms (e.g., N-ethylcarbamoyloxy, N-phenylcarbamoyloxy), a silyloxy group having preferably from 1 to 50 carbon a toms (e.g. trimethylsilyloxy, dibutylmethylsilyloxy), an alkyl- or aryl-sulfonyloxy group having preferably from 1 to 70 , more preferably from 1 to 50, total carbon a toms (e.g., dodecylsulfonyloxy), an acylamino group having preferably from 2 to 70, more preferably from 2 to 50 total carbon atoms (e.g., acetamido, benzamido, tetradecanamido, 2-(2,4-tert-amylphenoxyacetamido, 2-[4-(4-hydroxyphenylsulfonyl) phenoxy)]decanamido, isopentadecanamido, 2-(2,4-di-t-amylphenoxy)-butanamido, 4-(3-t-butyl-4-hydroxyphenoxy) butanamido), an alkylamino group having preferably from 1 to 70, more preferably from 1 to 50 total carbon atoms (e.g., methylamino, butylamino, dodecylamino, dimethylamino, diethylamino, methylbutylamino), an arylamino group having preferably from 6 to 70, more preferably from 6 to 50 total carbon atoms (e.g., phenylamino, 2-chloroanilino, 2-chloro-5-tetradecanamidoanilino, N-acetylanilino, 2-chloro-5-[α-2-tert-butyl-4-hydroxyphenoxy)dodecanamido]anilino, 2-chloro-5-dodecyloxycarbonylanilino), a ureido group having preferably from 2 to 70, more preferably from 2 to 50 total carbon atoms (e.g., methylureido, phenylureido, N,N-dibutylureido, dimethylureido), a sulfamoylamino group having preferably from 1 to 70, more preferably from 1 to 50 total carbon atoms (e.g., N,N-dipropylsulfamoylamino, N-methyl-N-decylsulfamoylamino), an alkenyloxy group having preferably from 2 to 70, more preferably from 2 to 50 total carbon atoms (e.g., 2-propenyloxy, a formyl group), an alkyl-, aryl- or heterocyclic-acyl group having preferably from 1 to 70, more preferably from 1 to 50 carbon atoms (e.g., acetyl, benzoyl, 2,4-di-tert-amylphenylacetyl, 3-phenylpropanoyl, 4-dodecyloxybenzoyl), an alkyl-, aryl- or heterocyclic-sulfonyl group having preferably from 1 to 70, more preferably from 1 to 50 carbon atoms (e.g., methanesulfonyl, octanesulfonyl, benzenesulfonyl, toluenesulfonyl), a sulfinyl group having preferably from 1 to 70, more preferably from 1 to 50 carbon atoms octanesulfinyl, dodecylsulfinyl, dodecanesulfinyl, phenylsulfinyl, 3-pentadecylphenylsulfinyl, 3-phenoxypropylsulfinyl), an alkyl-, aryl- or heterocyclicoxycarbonyl group having preferably from 2 to 70, more preferably from 2 to 50 total carbon atoms (e.g., methoxycarbonyl, butoxycarbonyl, dodecyloxycarbonyl, octadecyloxycarbonyl, phenyloxycarbonyl, 2-pentadecyoxycarbonyl), an alkyl-, aryl- or heterocyclicoxycarbonylamino group having preferably from 2 to 70, more preferably from 2 to 50 total carbon atoms- (e.g., methoxycarbonylamino, tetradecyloxycarbonylamino, phenoxycarbonylamino, 2,4-di-tert-butylphenoxycarbonylamino), a sulfonamido group having preferably from 1 to 70, more preferably from 1 to 50 carbon atoms (e.g., methanesulfonamido, hexadecansulfonamido, benzenesulfonamido, p-toluenesulfonamido, octadecanesulfonamido, 2-methoxy-5-tert-butylbenzenesulfonamido), a carbamoyl group having preferably from 1 to 70, more preferably from 1 to 50 carbon atoms (e.g., N-ethylcarbamoyl, N,N-dibutylcarbamoyl, N-(2-docecyloxyethyl)carbamoyl, N-methyl-N-dodecylcarbamoyl, N-[3-(2,4-di-tert-amylphenoxy)-propyl]carbamoyl), a sulfamoyl group having preferably from 0 to 70, more preferably from 1 to 50 carbon atoms (e.g., N-ethylsulfamoyl, N,N-dipropylsulfamoyl, N-(2-dodecyloxyethyl)sulfamoyl, N-ethyl-N-dodecylsulfamoyl, N,N-diethylsulfamoyl), a phosphonyl group having from 1 to 70, more preferably from 1 to 50 total carbon atoms (e.g., phenoxyphosphonyl, octyloxyphosphonyl, phenylphosphonyl), a sulfamido group (e.g., dipropylsulfamoylamino), an imido group having from 1 to 70, more preferably from 1 to 50 total carbon atoms (e.g., N-succinimido, N-hydantoinyl, N-phthalimido, 3-octadecenylsuccinimido), an azolyl group (e.g., imidazolyl, pyrazolyl, 3-chloro-pyrazol-1-yl, triazolyl); a hydroxyl group, a cyano group; a carboxyl group; a nitro group, a sulfo group, and an unsubstituted amino group.

$R_{31}$ and $R_{41}$ each is preferably a halogen atom, an alkyl group, an alkoxy group, an acylamino group, an anilino group, a ureido group, a sulfonamido group, a carbamoyl group, a sulfamoyl group or a carboxyl group.

$R_{11}$ is preferably a branched or cyclic alkoxy group or a substituted aryloxy group, and most preferably unsubstituted branched alkoxy group.

In formula (I), $R_{21}$ represents a substituent. As Examples of the substituent represented by $R_{21}$ include those substituents represented by $R_{31}$ or $R_{41}$. $R_{21}$ may be an aryl group having a substituent at least at the ortho-position thereof. $R_{21}$ is preferably an alkyl group, an aryl group, a carbamoyl group, an acylamino group or a ureido group and more preferably an aryl group, especially preferably

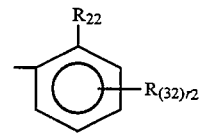

group defined in the formula (II) .

Compounds of formula (II) are described in detail hereunder.

$R_{12}$ represents an aliphatic group, an aryl group, a heterocyclic group, an alkoxy group, an aryloxy group, an alkylamino group, an arylamino group, a heterocyclic-oxy group or a heterocyclic-amino group, which may optionally be substituted by one or more substituents. These substituents include those previously mentioned as being represented by $R_{31}$ or $R_{41}$.

$R_{12}$ is more precisely an aliphatic group example, an alkyl, aralkyl, alkenyl, alkynyl, cycloalkyl or cycloalkenyl group having from 1 to 32 carbon atoms, such as methyl, ethyl, propyl, tridecyl, 2-methanesulfonylethyl, 3-(3-pentadecylphenoxy)propyl, 3-{4-{2-[4-(4-hydroxyphenylsulfonyl)phenoxy]dodecanamido}phenyl}propyl, 2-ethoxytridecyl, trifluoromethyl, cyclopentyl, 3-(2,4-di-t-amylphenoxy)propyl); an aryl group having preferably from 6 to 40 total carbon atoms ( for example, phenyl butylphenyl, 2,4-di-t-amylphenyl, 4-tetradecanamidophenyl), a 5- to 9-membered heterocyclic group containing at least one of a nitrogen, oxygen and sulfur atoms as a hereto atom and from 1 to 40 total carbon atoms, preferably 5- or 6-membered heterocyclic group containing a nitrogen atom as a hetero atom (for example, 2-furyl, 2-thienyl, 2-pyrimidinyl, 2-benzothiazolyl) , an alkoxy group having preferably from 1 to 32 carbon atoms, which may be straight or branched chain or cyclic moiety (for example, methoxy, ethoxy, 2-methoxyethoxy, 2-dodecylethoxy, 2-methanesulfonylethoxy), an aryloxy group having preferably from 6 to 40 total carbon atoms (for example, phenoxy, 2-methylphenoxy, 4-t-butylphenoxy, 3-nitrophenoxy, 3-t-butyloxycarbamoylphenoxy, 3-methoxycarbamoyl), an alkylamino group having preferably from 1 to 32 carbon atoms, which may be straight or branched chain or cyclic moiety (for example, methylamino, butylamino, dodecylamino, diethylamino, methylbutylamino), an arylamino group having preferably from 6 to 40 total carbon atoms (for example, phenylamino, 2-chloroanilino, 2-chloro-5-tetradecanaminoanilino, 2-chloro-5-dodecyloxycarbonylanilino, N-acetylanilino, 2-chloro-5-{2-(3-t-butyl-4-hydroxyphenoxy)-dodecanamido)anilino), a heterocyclic-oxy group containing at least one of a nitrogen, oxygen and sulfur atoms as a hetero atom and from 1 to 40 total carbon atoms, preferably 5- or 6-membered heterocyclic group containing a nitrogen atom as a hetero atom ( for example, 1-phenyltetrazol-5-oxy, 2-tetrahydropyranyloxy) , or heterocyclic-amino group containing at least one of a nitrogen, oxygen and sulfur atoms as a hetero atom and from 1 to 40 total carbon atoms, preferably 5- or 6-membered heterocyclic group containing a nitrogen atom as hetero atom (for example, pyranyl-2-amino).

In the present invention, $R_{12}$ is preferably an alkyl group, an aryl group, an alkoxy group, an aryloxy group, an acylamino group, an alkylamino group, or an anilino group. More preferably, $R_{12}$ is an alkoxy group, an aryloxy group, an alkylamino group or an anilino group. Especially preferably, $R_{12}$ is a branched or cyclic alkoxy groups or a substituted aryloxy group in $R_{11}$ of formula (I).

The substituents represented by $R_{22}$ and $R_{32}$ include those previously mentioned as being represented by $R_{31}$ or $R_{41}$.

In formula (II), $R_{22}$ is as defined in $R_{31}$ or $R_{41}$ in formula (IV) or (V) and preferably an alkyl group, an aryl group, a heterocyclic group, an alkoxy group, an aryloxy group, an acylamino group, an alkylamino group, an anilino group, a ureido group, a sulfamoylamino group, an alkylthio group, an arylthio group, an alkoxycarbonylamino group, a sulfonamido group, a carbamoyl group, a sulfamoyl group, a sulfonyl group, a heterocyclic-oxy group, an acyloxy group, a carbamoyloxy group, an aryloxycarbonylamino group, an imido group, a heterocyclic-thio group, or a sulfinyl group.

$R_{22}$ is more preferably an alkyl group, an alkoxy group, an acylamino group, a sulfonamido group, a halogen atom, a ureido group, an alkylamino group, an anilino group, or a carbamoyl group. $R_{22}$ is especially preferably an alkoxy group, an ureido group, an alkylamino group or an anilino group, and most preferably an alkoxy group.

In formula (II), $R_{32}$ is preferably a halogen atom, an alkyl group, an aryl group, a heterocyclic group, an alkoxy group, an aryloxy group, an acylamino group, an alkylamino group, an anilino group, a ureido group, a sulfamoylamino group, an alkylthio group, an arylthio group, an alkoxycarbonylamino group, a sulfonamido group, a carbamoyl group, a sulfamoyl group, a sulfonyl group, an alkoxycarbonyl group, a heterocyclic-oxy group, an acyloxy group, a carbamoyloxy group, an aryloxycarbonylamino group, an imido group, a heterocyclic-thio group, a sulfinyl group, a phosphonyl group, an aryloxycarbonyl group, an acyl group, or an azolyl group. $R_{32}$ is more preferably a halogen atom, an acylamino group, an ureido group, or a sulfamoyl group, and especially preferably an acylamino group or a sulfamoyl group.

The compounds of formula (III) are described below.

In formula (III), $R_{13}$, $R_{23}$ and $R_{33}$ each represents a hydrogen atom or a substituent, provided that the total of Taft's substituent constant $\sigma^*$ values of $R_{13}$, $R_{23}$ and $R_{33}$ is 1.5 or more.

The Taft's substituent constant $\sigma^*$ value (hereinafter referred to as the $\sigma^*$ value) is one which is widely used as a barometer for quantitatively expressing the influence of a substituent on the reaction or equilibrium of an aliphatic compound. The $\sigma^*$ value is described in, for example, Taft, R. W., Jr., *Steric Effects in Organic Chemistry* (M. S. Newman, Ed), John Wiley, New York (1956), pages 556 to 675.

$\sigma^*$ values of typical substituents are mentioned below.

TABLE 1

| Substituent | $\sigma^*$ value | Substituent | $\sigma^*$ value | Substituent | $\sigma^*$ value |
|---|---|---|---|---|---|
| H | +0.49 | $CF_3$ | +2.61 | $COC_6H_5$ | +2.20 |
| F | +3.21 | $CCl_3$ | +2.65 | $COCF_3$ | +3.70 |
| CL | +2.96 | $CH_2CN$ | +1.30 | $CONH_2$ | +1.68 |

TABLE 1-continued

| Substituent | $\sigma^*$ value | Substituent | $\sigma^*$ value | Substituent | $\sigma^*$ value |
|---|---|---|---|---|---|
| CN | +3.30 | $CH_2CF_3$ | +0.92 | $CH_2CONH_2$ | +0.30 |
| $C_2H_5$ | −0.10 | $CO_2CH_3$ | +2.00 | $CH_2CO_2CH_3$ | +1.06 |
| $C_3G_7$-i | −0.19 | $CO_2C_2H_5$ | +2.20 | $CH_2CO_2C_2H_5$ | +0.82 |
| $C_4H_9$-t | −0.30 | $COCH_3$ | +1.65 | $CH_2SO_2CH_3$ | +2.65 |
| $C_6H_5$ | +0.60 | $SO_2CH_3$ | +3.68 | $NHCOCH_3$ | +1.40 |
| COOH | +2.08 | $SOCH_3$ | +3.24 | $CONHC_6H_5$ | +1.56 |

In the present invention, the substituents represented by $R_{13}$, $R_{23}$ and $R_{33}$ are not limited to the above-mentioned substituents or to the substituents described in the above-mentioned literature each having the disclosed $\sigma^*$ value, but include any others having a combined $\sigma^*$ value falling within the defined range.

In formula (III), the respective $\sigma^*$ value of $R_{13}$, $R_{23}$ and $R_{33}$ is not specifically defined, provided that the total of the combined $\sigma^*$ values falls within the defined range. $R_{13}$, $R_{23}$ and $R_{33}$ each represents a hydrogen atom or a substituent. Examples of these substituents include those previously mentioned as being represented by $R_{31}$ or $R_{41}$. As a matter of course, where $—C(R_{13})(R_{23})(R_{33})$ forms a branched alkyl group, it may be included in formula (I). $R_{13}$, $R_{23}$ and $R_{33}$ each preferably a hydrogen atom, a halogen atom, a cyano group, an alkyl group having from 1 to 36 carbon atoms, an aryl group having from 6 to 36 carbon atoms, an acyl group having from 1 to 36 carbon atoms, an alkoxycarbonyl group having from 2 to 36 carbon atoms, a carbamoyl group having from 1 to 36 carbon atoms, an acylamino group having from 1 to 36 carbon atoms, a sulfinyl group having from 1 to 36 carbon atoms, a sulfonyl group having from 1 to 36 carbon atoms.

Specific examples of combinations of $R_3$, $R_{23}$ and $R_{33}$, as well as the total $\sigma^*$ values thereof are shown below. However, the present invention is not limited to only them.

TABLE 2

| Substituent | Substituent | Substituent | Total of $\sigma^*$ values of Substituents |
|---|---|---|---|
| H | H | $CO_2C_2H_5$ | +3.10 |
| H | H | CN | +4.28 |
| H | H | $CONH_2$ | +2.66 |
| H | H | $CONHC_6H_5$ | +2.54 |
| H | H | $CH_2CN$ | +2.28 |
| H | H | $CH_2SO_2CH_3$ | +4.66 |
| H | H | $CH_2CCl_3$ | +1.73 |
| H | H | $CCl_3$ | +3.63 |
| H | H | $NHCOCH_3$ | +2.38 |
| H | H | $CF_3$ | +2.99 |
| H | $C_6H_5$ | $COC_6H_5$ | +3.29 |
| H | $CH_3$ | $COCH_3$ | +2.14 |
| H | $C_6H_5$ | $C_6H_5$ | +1.69 |
| $C_6H_5$ | $C_6H_5$ | $C_6H_5$ | +1.80 |

In the present invention, the total of $\sigma^*$ values of the substituents of $R_{13}$, $R_{23}$ and $R_{33}$ is more preferably 1.8 or more, especially preferably 2.0 or more. The upper limit of the total $\sigma^*$ values of these substituents is preferably about 7.0, more preferably about 6.0 and especially preferably about 5.0.

In formula (III), $R_{43}$ represents a substituent. Examples of the substituent include those previously mentioned as being presented by $R_{31}$ or $R_{41}$. $R_{43}$ is as defined in $R_{31}$ or $R_{41}$ in formula (IV) or (V) and may be an aryl group having a substituent at least at the orthoposition thereof. $R_{43}$ is preferably an alkyl group, an aryl group, a carbamoyl group, an acylamino group or a ureido group and is more preferably an aryl group, and especially preferably

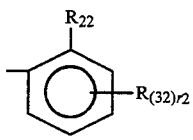

in formula (II).

In formulae (I), (II) and (III), $X_1$, $X_2$ and $X_3$ each represents a hydrogen atom or a group which is capable of splitting of from the formula when the coupler is reacted with an oxidation product of an aromatic primary amine color developing agent (the group is hereinafter simply referred to as a split-off group). When X shows the split-off group typical examples thereof include a halogen atom and an aromatic azo group, as well as a group bonded to an alkyl group, an aryl group, a heterocyclic group, an alkyl-, aryl- or heterocyclic-sulfonyl group, an alkyl-, aryl- or heterocyclic-sulfinyl group, or an alkyl-, aryl- or heterocyclic-carbonyl group and which is bonded to the coupling position via an oxygen, nitrogen, sulfur or carbon atom. The split-off group may also be a heterocyclic group bonded to the coupling position via a nitrogen atom. For instance, it includes a halogen atom, an alkoxy group, an aryloxy group, an acyloxy group, an alkyl- or arylsulfonyloxy group, an acylamino group, an alkyl- or arylsulfonamido group, an alkoxycarbonyloxy group, an aryloxycarbonyloxy group, an alkyl-, aryl- or heterocyclicthio group, a carbamoylamino group, a 5-membered or 6-membered heterocyclic group, an imido group, and an arylazo group. The alkyl, aryl or heterocyclic moiety in the split-off group may optionally be substituted by one or more substituents. Where it has two or more substituents, they may be same or different. These substituents each may further be substituted by one or more substituents, such those previously mentioned as being represented by $R_{31}$ or $R_{41}$.

More precisely, the split-off group includes a halogen atom (e.g., fluorine, chlorine, bromine), an alkoxy group (e.g., ethoxy, dodecyloxy, methoxyethylcarbamoylmethoxy, carboxypropyloxy, methylsulfonylethoxy, ethoxycarbonylmethoxy), an aryloxy group (e.g., 4-methylphenoxy, 4-chlorophenoxy, 4-methoxyphenoxy, 4-carboxyphenoxy, 3-ethoxycarboxyphenoxy, 3-acetylaminophenoxy, 2-carboxyphenoxy), an acyloxy group (e.g., acetoxy, tetradecanoyloxy, benzoyloxy), an alkyl- or aryl-sulfonyloxy group (e.g., methanesulfonyloxy, toluenesulfonyloxy), an acylamino group (e.g., dichloroacetylamino, heptafluorobutyrylamino), an alkyl- or aryl-sulfonamido group (e.g., methanesulfonamido, trifluoromethanesulfonamido, p-toluenesulfonylamino), an alkoxycarbonyloxy group (e.g., ethoxycarbonyloxy, benzyloxycarbonyloxy), an aryloxycarbonyloxy group (e.g., phenoxycarbonyloxy), an alkyl-, aryl- or heterocyclic-thio group (e.g., ethylthio, 2-carboxyethylthio, dodecylthio, 1-carboxydodecylthio, phenylthio, 2-butoxy-5-t-octylphenylthio, tetrazolylthio), a carbamoylamino group (e.g., N-methylcarbamoylamino, N-phenylcarbamoylamino), a 5-membered or 6-membered nitrogen-containing heterocyclic group (e.g., imidazolyl, pyrazolyl, triazolyl, tetrazolyl, 1,2-dihydro-2-oxo-1-pyridyl), an imido group (e.g., succinimido, hydantoinyl), and an arylazo group (e.g., phenylazo, 4-methoxyphenylazo). As matter of course, the split-off group may further be substituted by one or more substituents, such as those previously mentioned as being represented by $R_{31}$ ro $R_{41}$. Split-off groups bonded to the formula via a carbon atom are bis-type couplers obtained by condensation of aldehydes or ketones and 4-equivalent couplers. The split-off group of the present invention may contain a photographically useful group, for example, a development inhibitor or a development accelerator.

Preferred groups represented by $X_1$, $X_2$ or $X_3$ are a halogen atom, an alkoxy group, an aryloxy group, an alkyl- or aryl-thio group, and a 5-membered or 6-membered nitrogen-containing heterocyclic group bonded to the coupling active position via a nitrogen atom, more preferably a halogen atom or an aryl-thio group, and most preferably a chlorine atom.

The cyan couplers of formulae (I), (II) and (III) may be part of dimers or higher polymers in which the group represented by $R_{11}$, $R_{21}$ or $X_1$, the group represented by $R_{12}$, $R_{22}$ or $R_{32}$ or the group represented by $R_{13}$, $R_{23}$ or $R_{33}$, $R_{34}$ or $X_4$ is a divalent group or is bonded to a high molecular chain to form a homopolymer or a copolymer. Such homopolymers or copolymers in which that group is bonded to a high molecular chain are typically homopolymers or copolymers of ethylenically unsaturated compounds which form addition polymers having a cyan coupler residue of formula (I), (II) or (III). In that case, the homopolymers or copolymers each may have one or more cyan coloring repeating units each having a cyan coupler residue of formula (I), (II) or (III) in the polymer molecule and may contain one more non-coloring ethylenic monomers as the monomer or comonomer components. The cyan coloring repeating unit having a cyan coupler residue of formula (I), (II) or (III) is preferably represented by the following general formula (P):

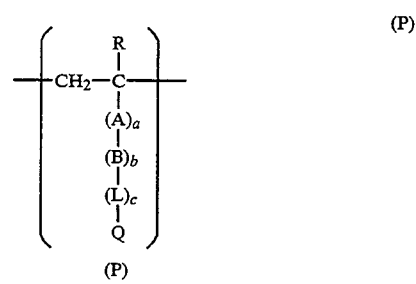

wherein R represents a hydrogen atom, an alkyl group having from 1 to 4 carbon atoms, or a chlorine atom;

A represents —CONH—, —COO—, or a substituted or unsubstituted phenylene group;

B represents a substituted or unsubstituted alkylene, phenylene or aralkylene group;

L represents —CONH—, —NHCONH—, —NHCOO—, —NHCO—, —OCONH—, —NH—, —COO—, —OCO—, —CO—, —O—, —S—, —SO$_2$—, —NHSO$_2$—, or —SO$_2$NH—;

a, b and c each represent 0 or 1; and

Q represents a cyan coupler derived from a compound of formula (I), (II) or (III) by removing a hydrogen atom from one of the groups represented by $R_{11}$, $R_{21}$ or $X_1$, one of the groups represented by $R_{12}$, $R_{22}$, $R_{32}$ or $X_2$ or one of the groups represented by $R_{13}$, $R_{23}$, $R_{33}$, $R_{43}$ or $X_3$, in the respective formulae.

Among the polymers, preferred are copolymers comprising cyan coloring monomers of coupler units of formula (I), (II) or (III) and non-coloring ethylenic monomers which do not couple with an oxidation product of an aromatic primary amine developing agent.

The non-coloring ethylenic monomers which do not couple with an oxidation product of an aromatic primary amine developing agent include, for example, acrylic acrid, α-chloroacrylic acid, α-alkylacrylic acids (e.g., methacrylic acid) and amides or esters derived from these acrylic acids (e.g., acrylamide, methacryiamide, n-butylacrylamide, t-butylacrylamide, diacetylacrylamide, methyl acrylate, ethyl acrylate, n-propyl acrylate, n-butyl acrylate, t-butyl acrylate, iso-butyl acrylate, 2-ethylhexyl acrylate, n-octyl acrylate, lauryl acrylate, methyl methacrylate, ethyl methacrylate, n-butyl methacrylate, β-hydroxy methacrylate), vinyl esters (e.g., vinyl acetate, vinyl propionate, vinyl laurate), acrylonitrile, methacrylonitrile, aromatic vinyl compounds (e.g., styrene and derivatives thereof, such as vinyl toluene, divinylbenzene, vinylacetophenone and sulfoethylene), iraconic acid, citraconic acid, crotonic acid, vinylidene chloride, vinyl alkyl ethers (e.g., vinyl ethyl ether), maleates, N-vinyl-2-pyrrolidone, N-vinylpyridine, and 2- and 4-vinylpyridines. Of them, especially preferred are acrylates, methacrylates and maleates.

In the present invention, the copolymers may contain two or more different non-coloring ethylenic monomers. For instance, the copolymer may be a combination of methyl acrylate and butyl acrylate, a combination of butyl acrylate and styrene, a combination of butyl methacrylate and methacrylic acid, or a combination of methyl acrylate and diacetoneacrylamide.

As is well known in the field of polymer couplers, ethylenically unsaturated comonomers to be copolymerized with vinyl monomers corresponding to the above-mentioned formulae (I), (II) or (III) are selected so that the physical and/or chemical properties of the copolymers formed therefrom, such as this solubility, this compatibility with binders of photographic compositions such as gelatin, this flexibility, as well as this thermal stability, are favorably influenced by the selected comonomers.

For incorporating the couplers of the present invention into silver halide photographic materials, preferably into the red-sensitive silver halide emulsion layers thereof, it is preferred that the couplers are in the form of a so-called coupler-in-emulsion. For this purpose, it is preferred that the total carbon number atoms in at least one of the groups represented by $R_{11}$, $R_{21}$ or $X_1$, the groups represented by $R_{12}$, $R_{22}$, $R_{32}$ or $X_2$ or the groups represented by $R_{13}$, $R_{23}$, $R_{33}$, $R_{43}$ or $X_3$ is from 10 to 50.

Next, specific examples of couplers of the present invention are shown below, which, however, are not intended to restrict the scope of the present invention.

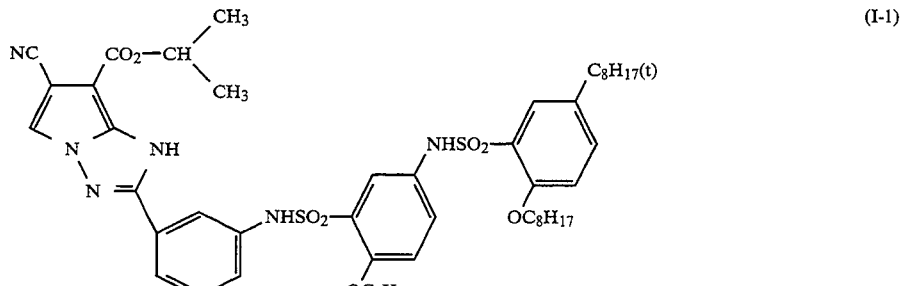

(I-1)

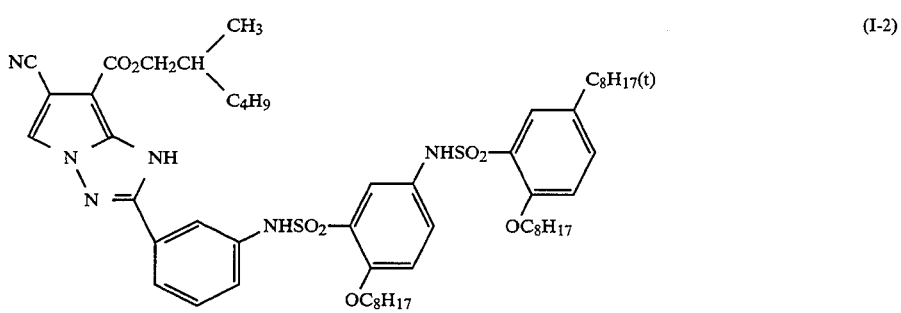

(I-2)

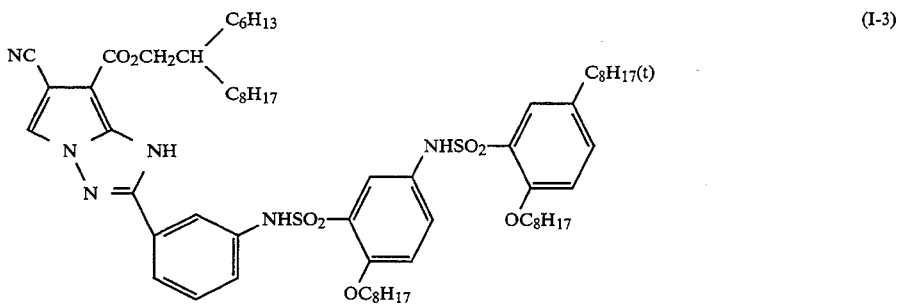

(I-3)

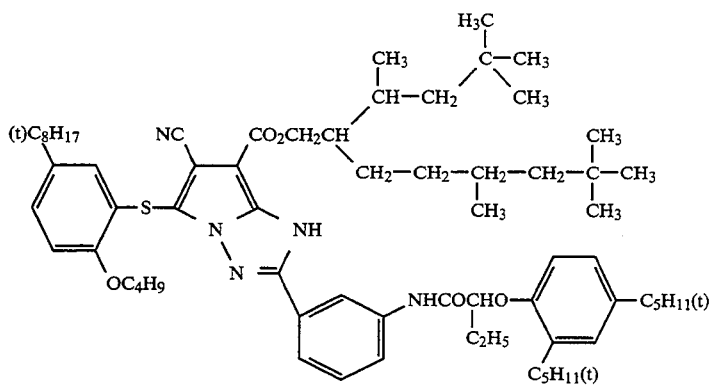
(I-4)
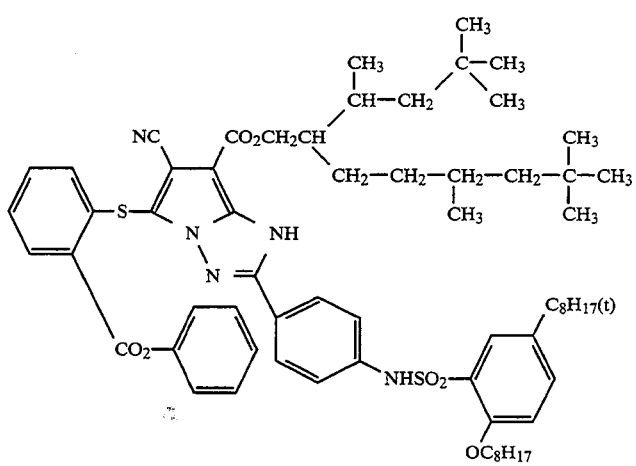
(I-5)
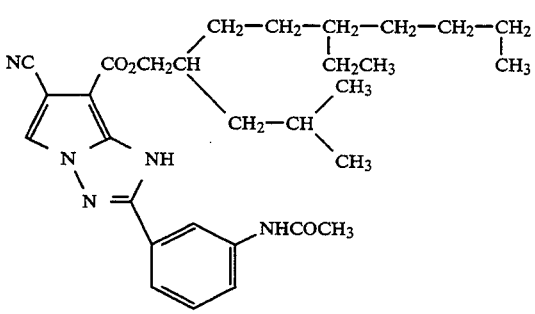
(I-6)
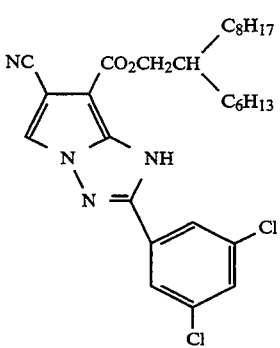
(I-7)

-continued
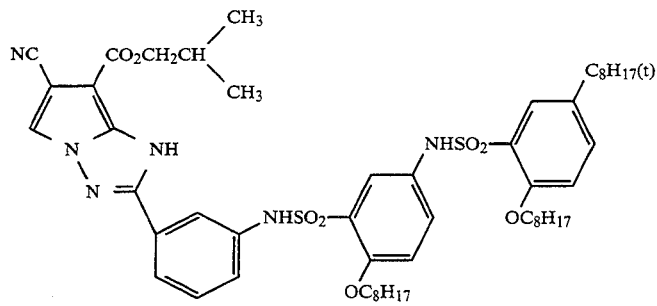
(I-8)
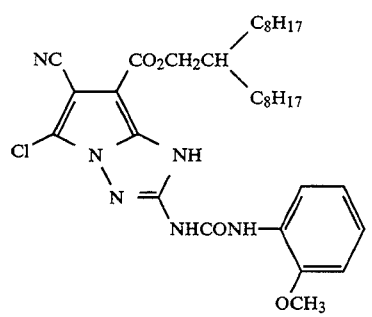
(I-9)
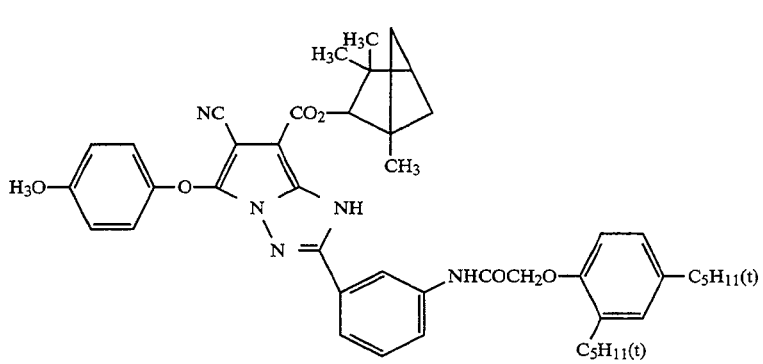
(I-10)
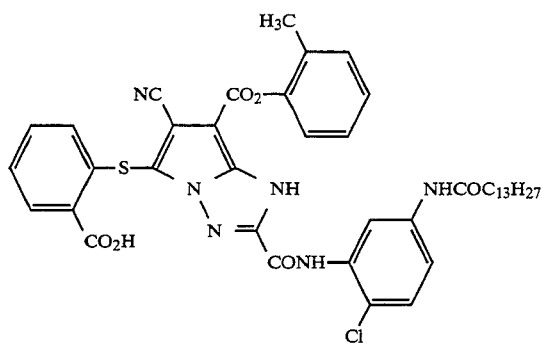
(I-11)
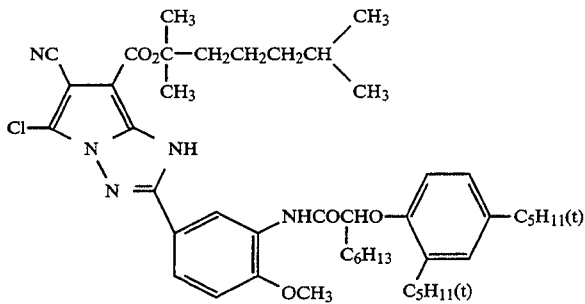
(I-12)

-continued
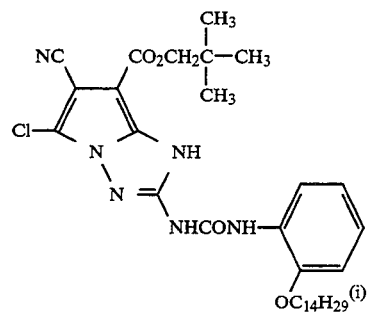
(I-13)
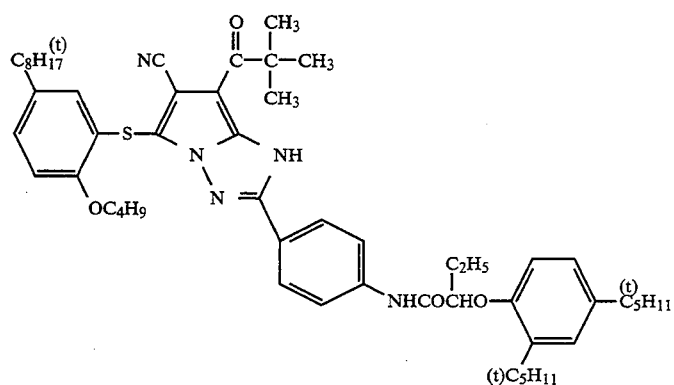
(I-14)
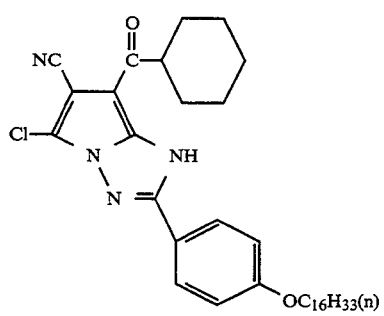
(I-15)
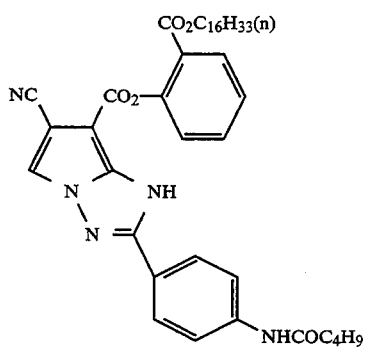
(I-16)

-continued
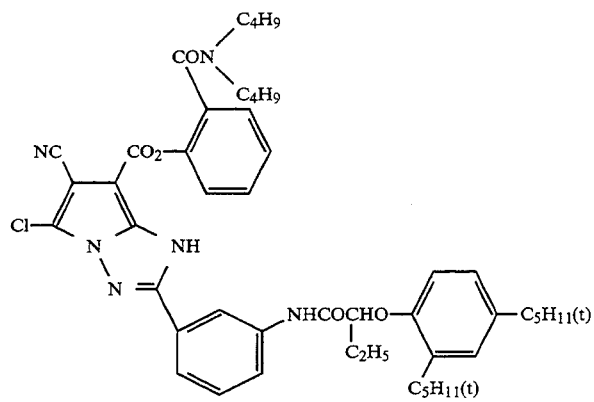
(I-17)
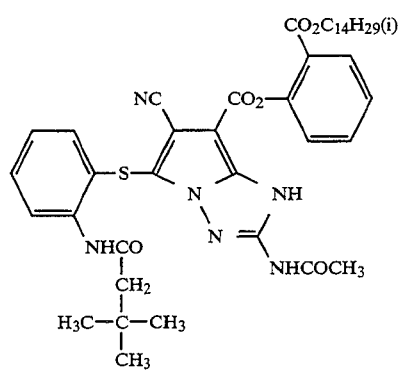
(I-18)
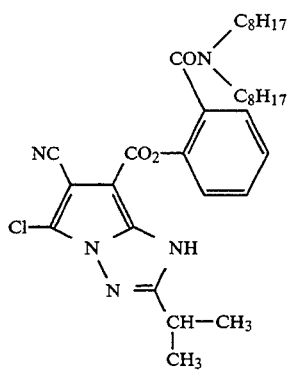
(I-19)
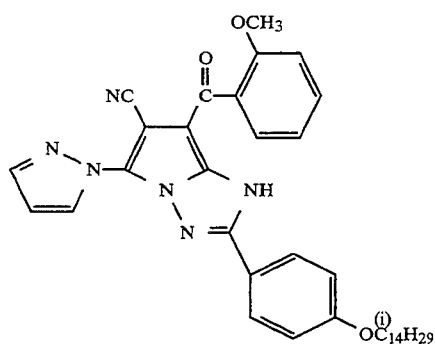
(I-20)

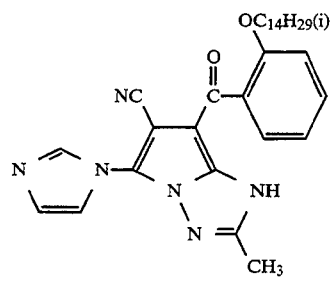
(I-21)
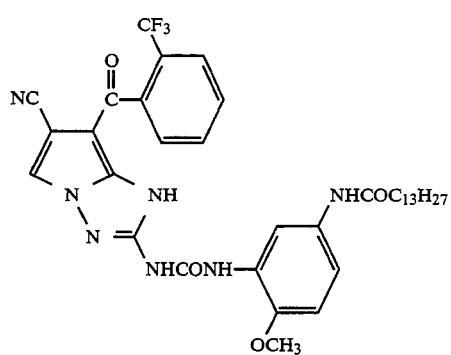
(I-22)
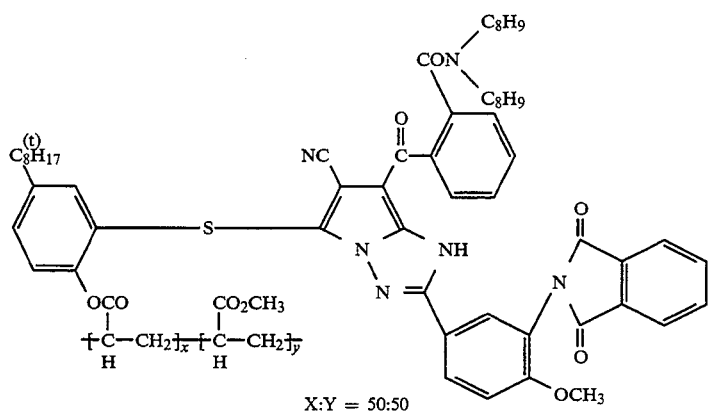
(I-23)
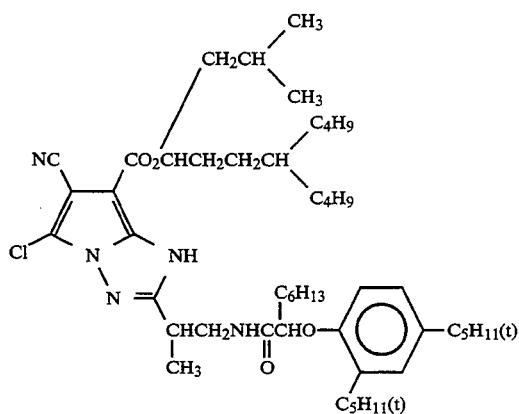
(I-24)

-continued
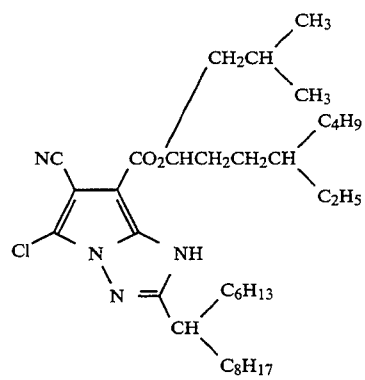 (I-25)
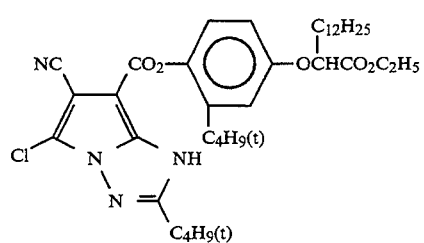 (I-26)
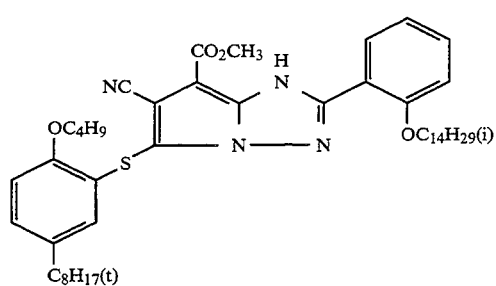 (II-1)
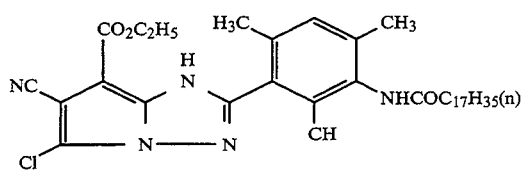 (II-2)
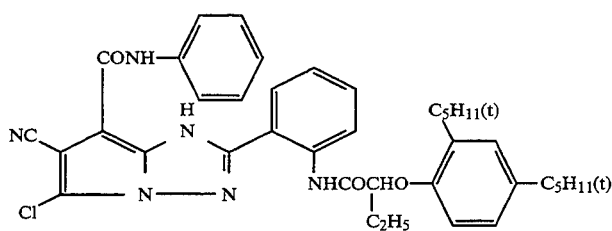 (II-3)
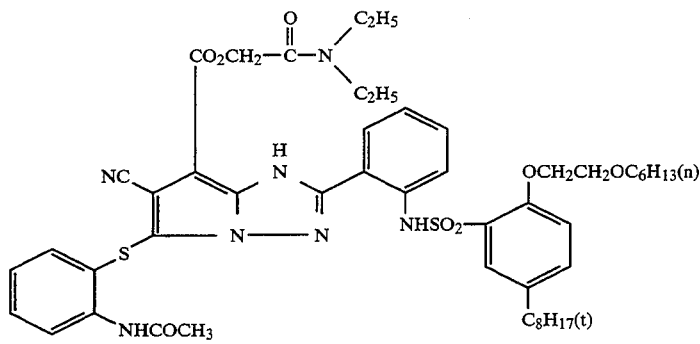 (II-4)

(II-5)
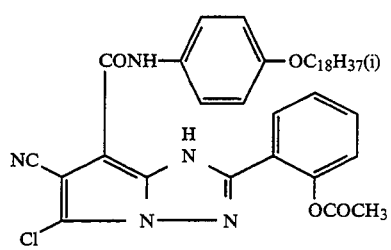
(II-6)
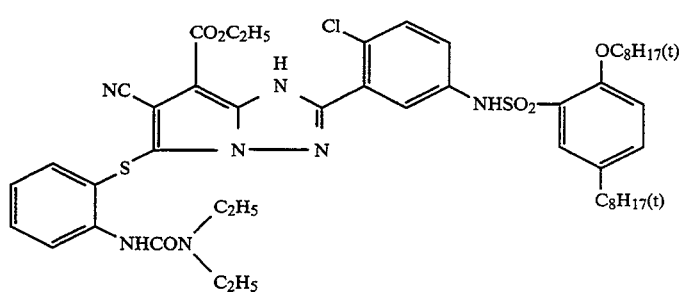
(II-7)
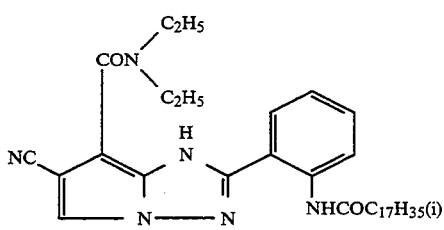
(II-8)
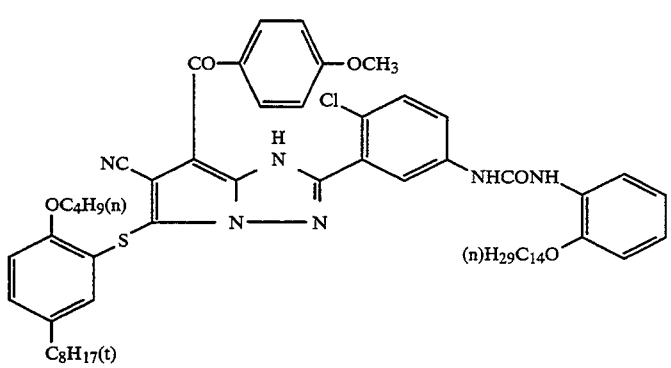
(II-9)
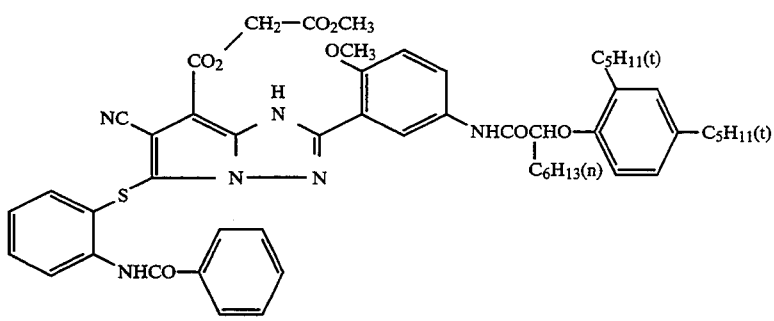

-continued
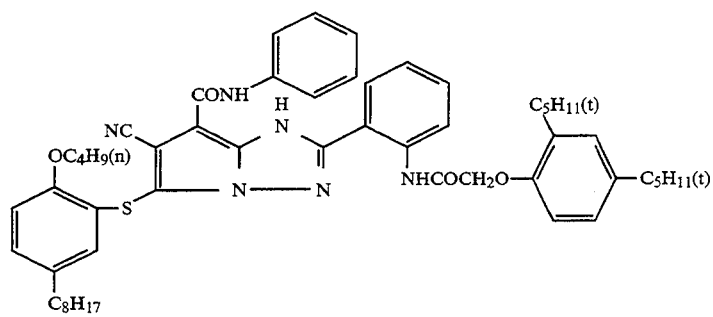 (II-10)
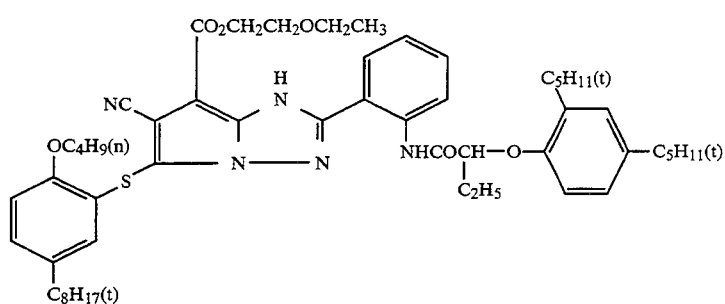 (II-11)
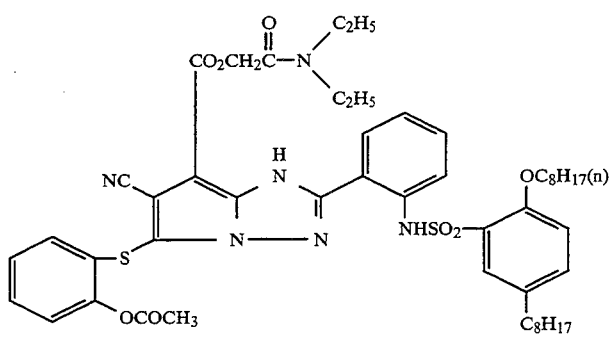 (II-12)
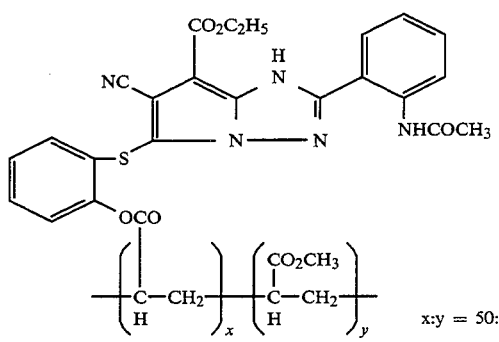 (II-13)
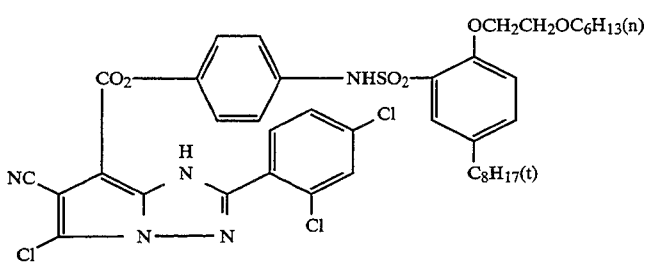 (II-14)

-continued
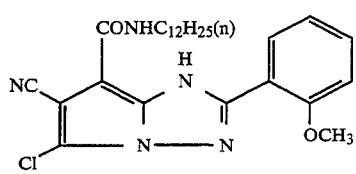
(II-15)
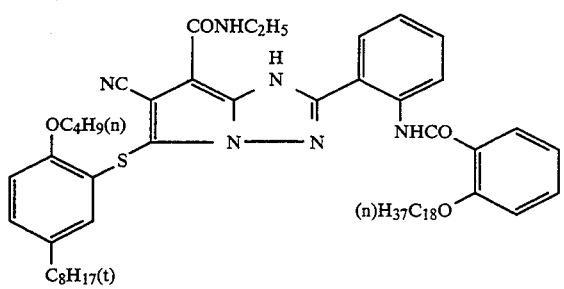
(II-16)
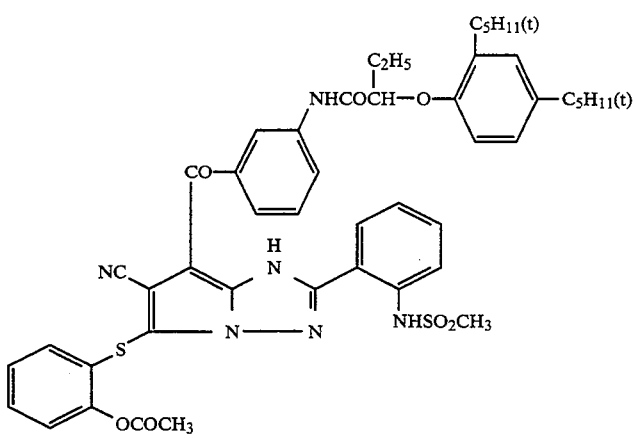
(II-17)
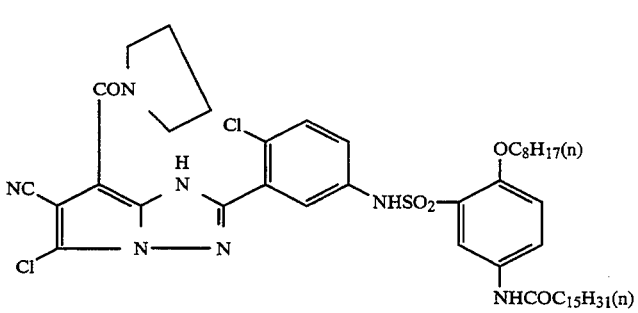
(II-18)
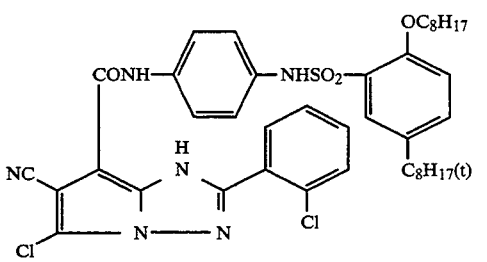
(II-19)

-continued
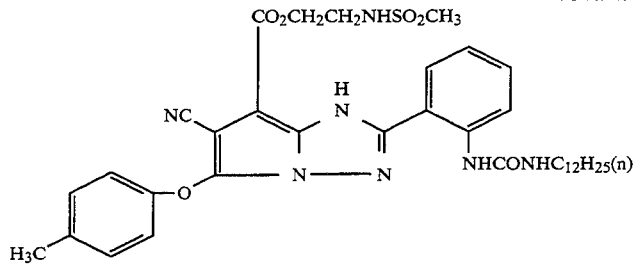
(II-20)
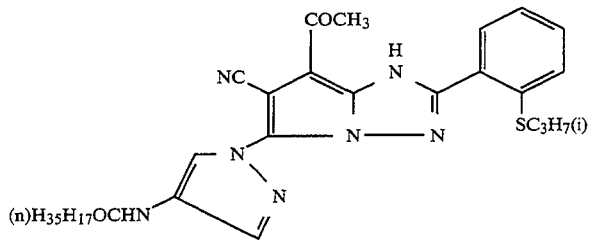
(II-21)
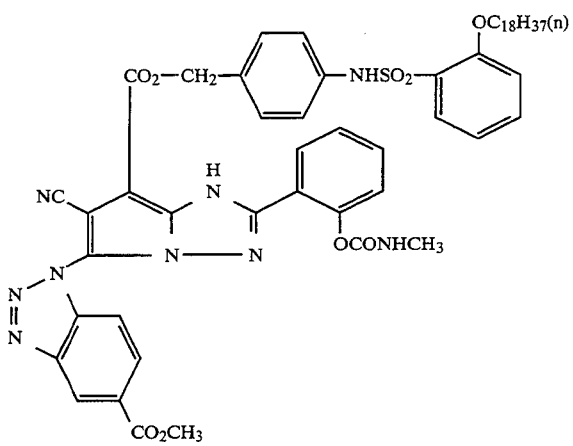
(II-22)
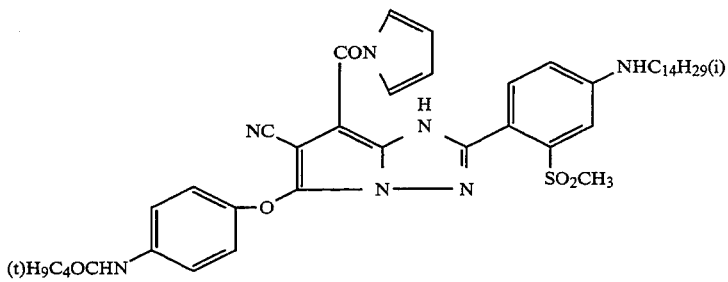
(II-23)
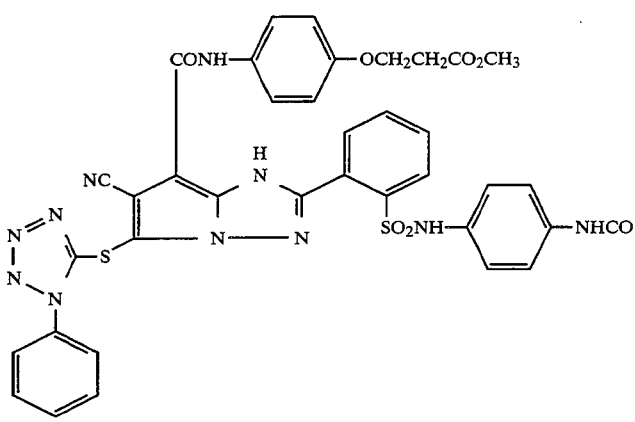
(II-24)

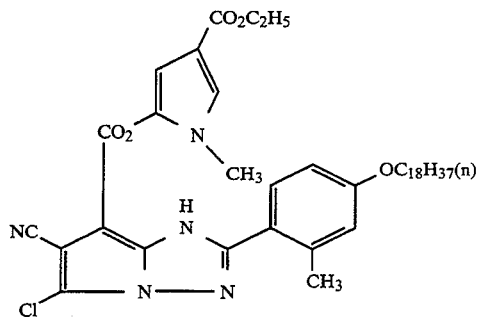 (II-25)
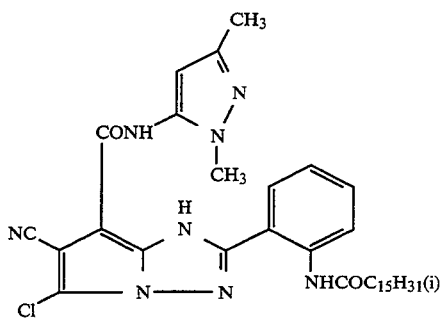 (II-26)
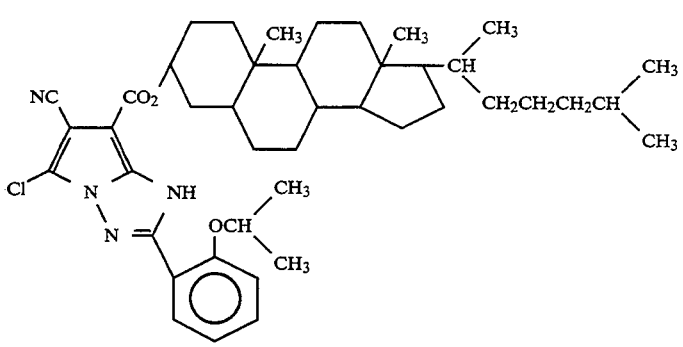 (II-27)
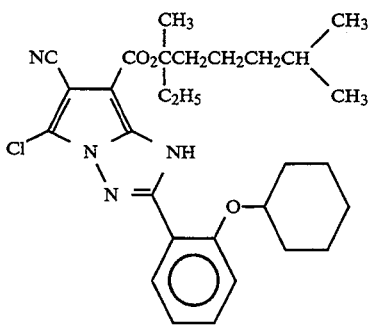 (II-28)
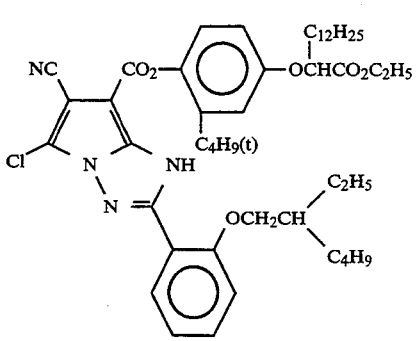 (II-29)

-continued
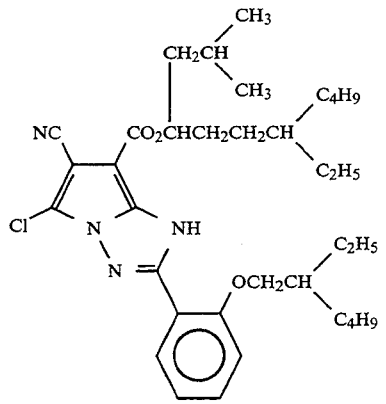 (II-30)
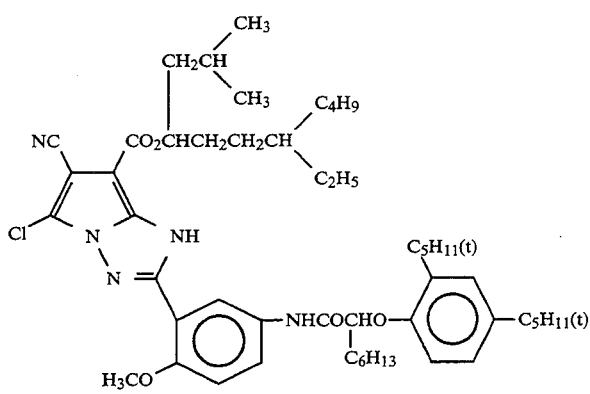 (II-31)
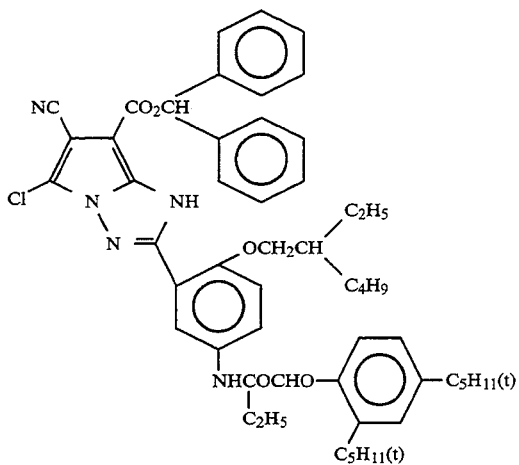 (II-32)
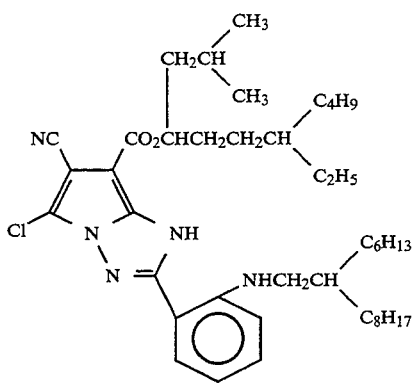 (II-33)

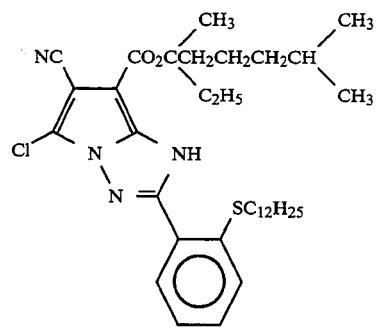
(II-34)
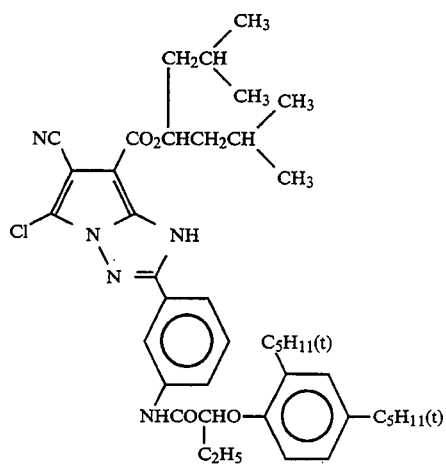
(II-35)
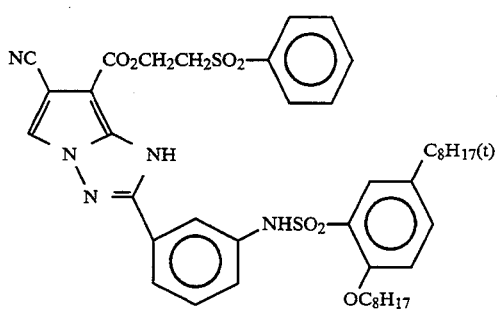
(III-1)
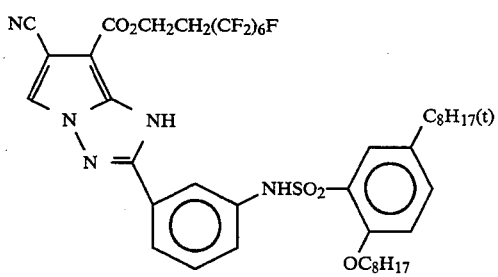
(III-2)
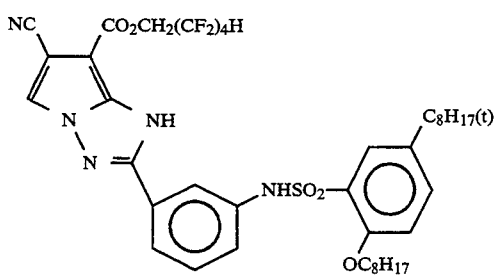
(III-3)

-continued
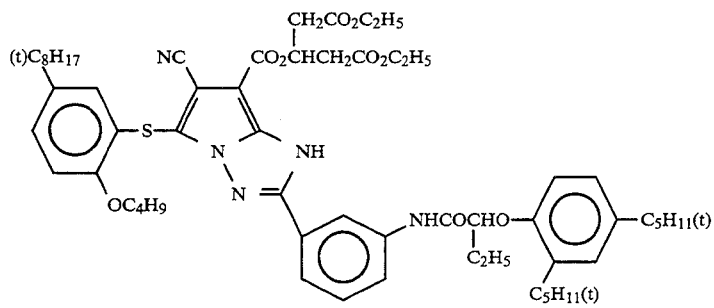
(III-4)
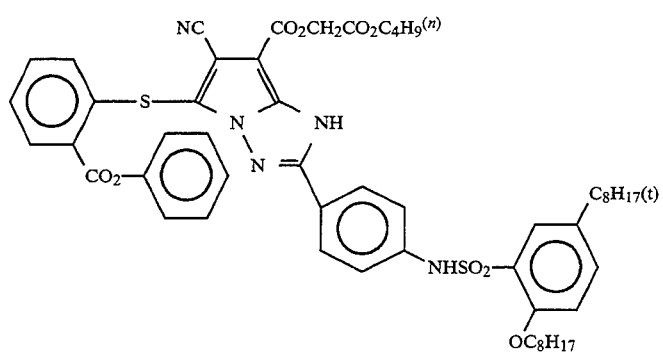
(III-5)
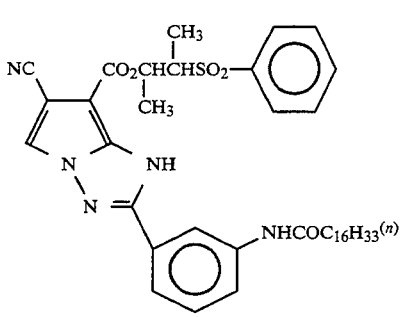
(III-6)
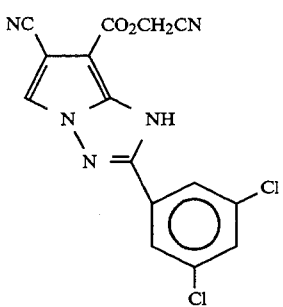
(III-7)
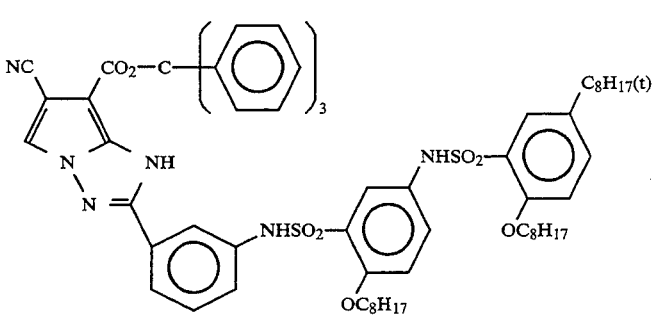
(III-8)

-continued
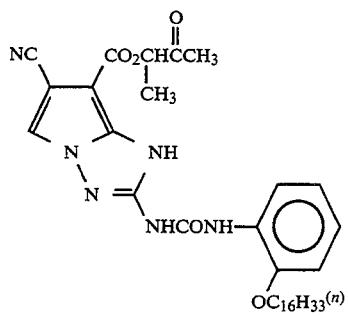
(III-9)
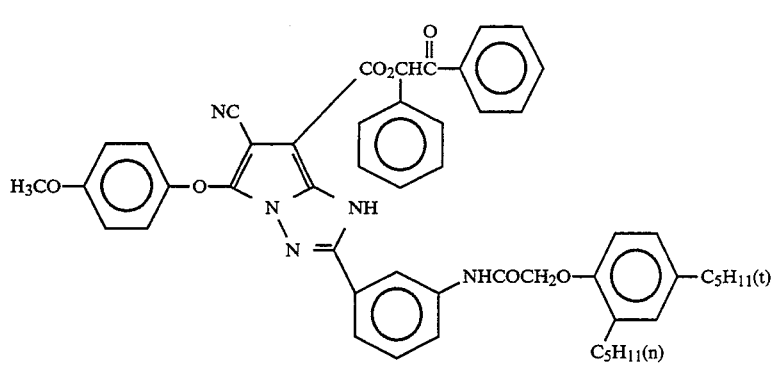
(III-10)
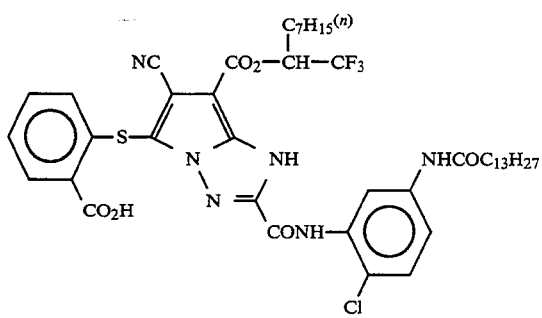
(III-11)
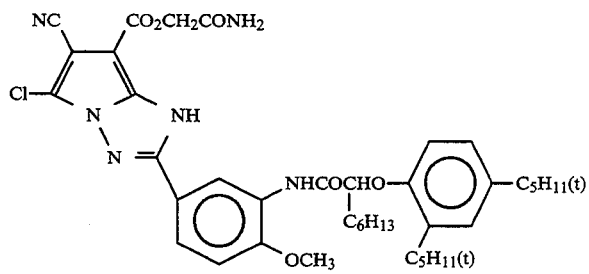
(III-12)
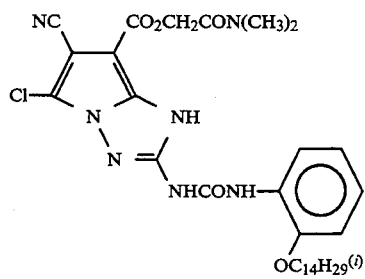
(III-13)

-continued
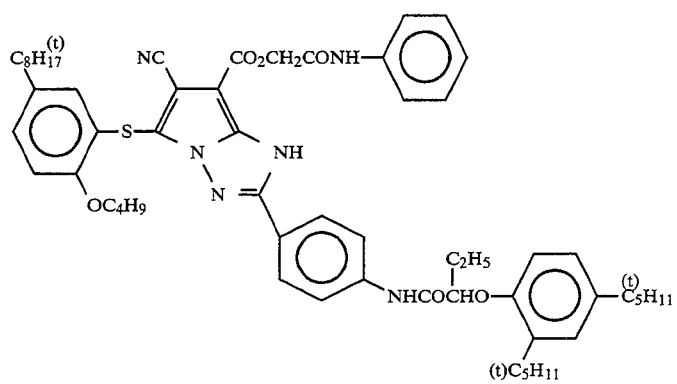
(III-14)
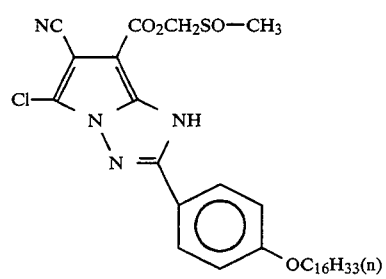
(III-15)
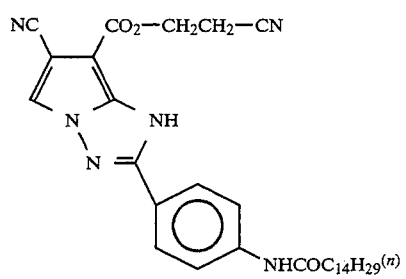
(III-16)
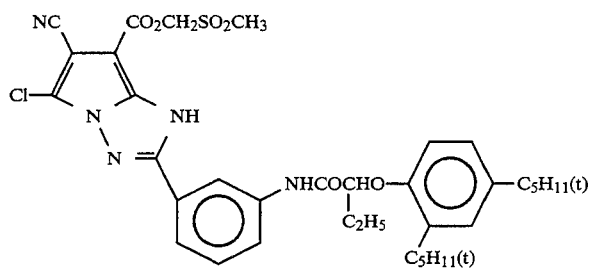
(III-17)
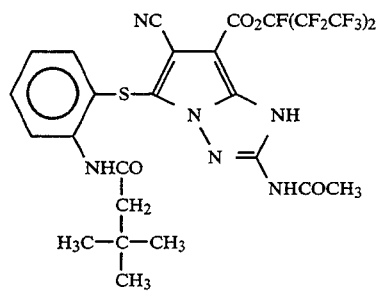
(III-18)

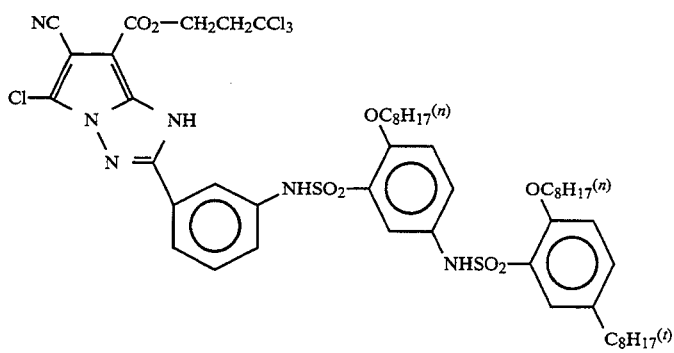
(III-19)
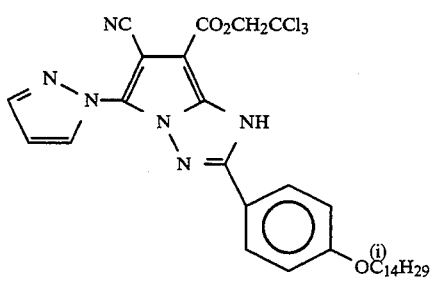
(III-20)
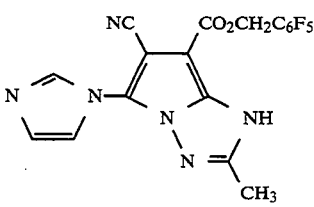
(III-21)
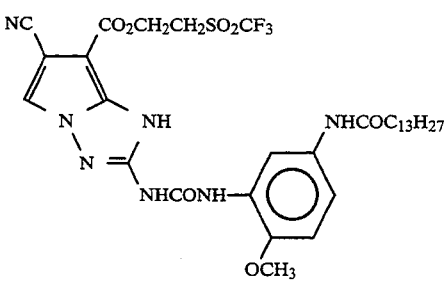
(III-22)
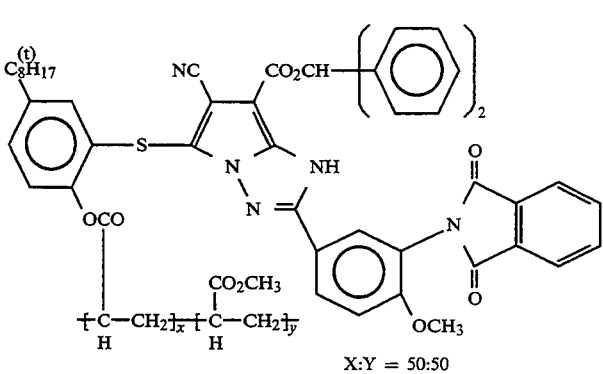
(III-23)

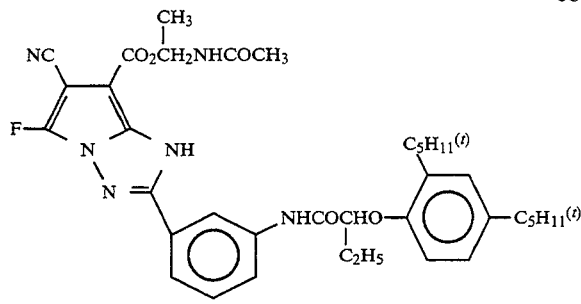

(III-24)

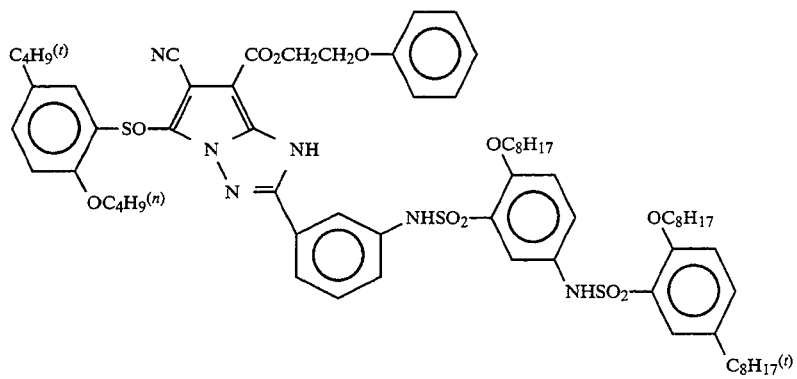

(III-25)

Intermediates of the couplers of the present invention can be produced by any known method. For instance, one may use the methods described in *J. Am. Chem. Soc.*, 112, 2465 (1990), *Org. Synth.*, I 270 (1941), *J. Am. Chem. Soc.*, 80, 5332 (1958), and *Rec. Tray. Chim.*, 80, 1075 (1961) and the methods described in the literature references referred to therein, as well as other methods analogous to the disclosed methods.

Next, some production examples of the couplers of the present invention are described below:

PRODUCTION EXAMPLE 1

Production of Coupler (I-7)

Coupler (I-7) was produced in accordance with the following reaction route:

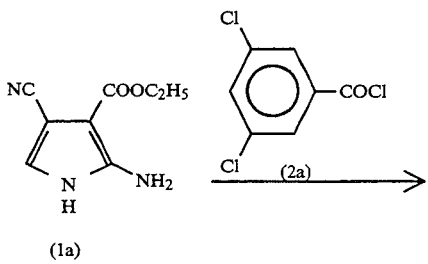

(1a)

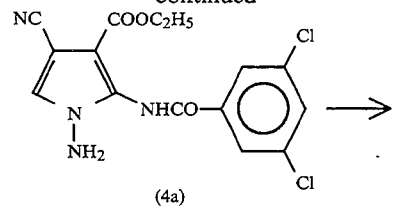

(2a)

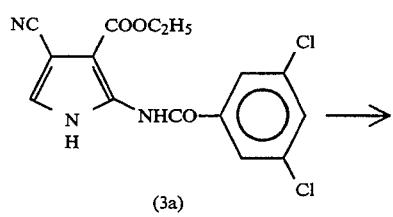

(3a)

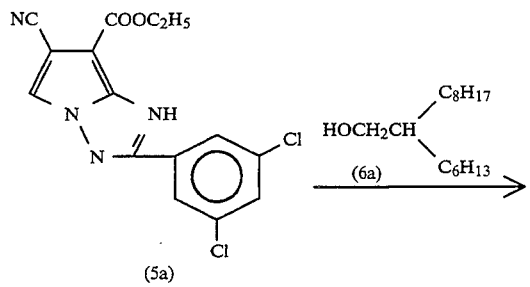

(4a)

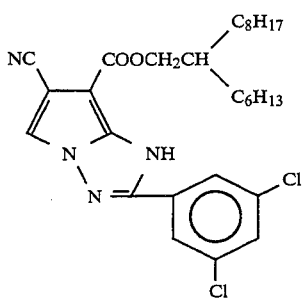

(5a)

(6a)

Coupler (I-7)

3,5-Dichlorobenzoyl chloride (2a) in the amount of 83.2 g (0.4 mol) was added to 300 ml of dimethylacetamide solution of 66.0 g (0.4 mol) of 2-amino-4-cyano-3-methoxycarbonylpyrrole (1a) at room temperature and stirred for 30 minutes. Water was added to this, which was then extracted two times, each time with ethyl acetate. The organic layers were combined, washed with water and a saturated saline solution and dried with anhydrous sodium sulfate. The solvent was removed from the combined layers by distillation under reduced pressure, and the residue was then recrystallized from 300 ml of acetonitrile to give 113 g (84%) of compound (3a).

A powder of 252 g (4.5 mol) of potassium hydroxide was added to 200 ml of dimethylformamide solution of 101.1 g (0.3 mol) of compound (3a) at room temperature and well stirred. After being cooled with water, 237 g (2.1 mol) of hydroxylamine-O-sulfonic acid was added thereto little by little with caution that the temperature did not rise rapidly. After the addition, the whole was stirred for 30 minutes. An aqueous 0.1N hydrochloric acid solution was dropwise added thereto so that the reaction system was neutralized under observation with a pH test paper. After being extracted three times each with ethyl acetate, the organic layer separated, was washed with water and a saturated saline solution, and dried with anhydrous sodium sulfate. The solvent was removed from the layer by distillation under reduced pressure and purified by column chromatography (with a developing solvent of hexane/ethyl acetate=2/1) to give 9.50 g (9%) of compound (4a).

Nine cc of carbon tetrachloride was added to 30 ml of acetonitrile solution of 7.04 g (20 mmol) of compound (4a) at room temperature. Subsequently 5.76 g (22 mmol) of triphenylphosphine was added thereto and heated under reflux for 8 hours. After cooled, water was added to this, which was then extracted three times, each time with ethyl acetate. The organic layer separated, was washed with water and a saturated saline solution, and dried with anhydrous sodium sulfate. The solvent was removed from the layer by distillation under reduced pressure and purified by column chromatography (with a developing solvent of hexane/ethyl acetate=4/1) to give 1.13 g (17%) of compound (5a).

The thus obtained compound (5a) in the amount of 1.8 g and 12.4 g of compound (6a) were dissolved in 2.0 ml of sulforane, and 1.5 g of titanium isopropoxide was added thereto. These were reacted for 1.5 hours while keeping the reaction temperature to be 110° C., and ethyl acetate was added to the reaction mixture, which was then washed with water. The ethyl acetate layer was dried and ethyl acetate was removed by distillation from the layer. Then, the residue was purified by column chromatography to give 1.6 g of the intended Coupler (I-7).

This had a melting point of 97 to 98° C.

PRODUCTION EXAMPLE 2

Production of Compound (II-1)

Compound (II-1) was produced in accordance with the following reaction route:

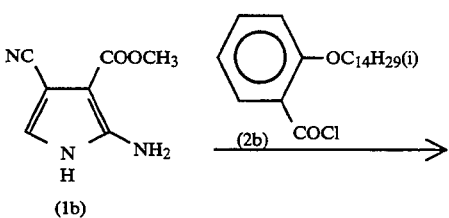

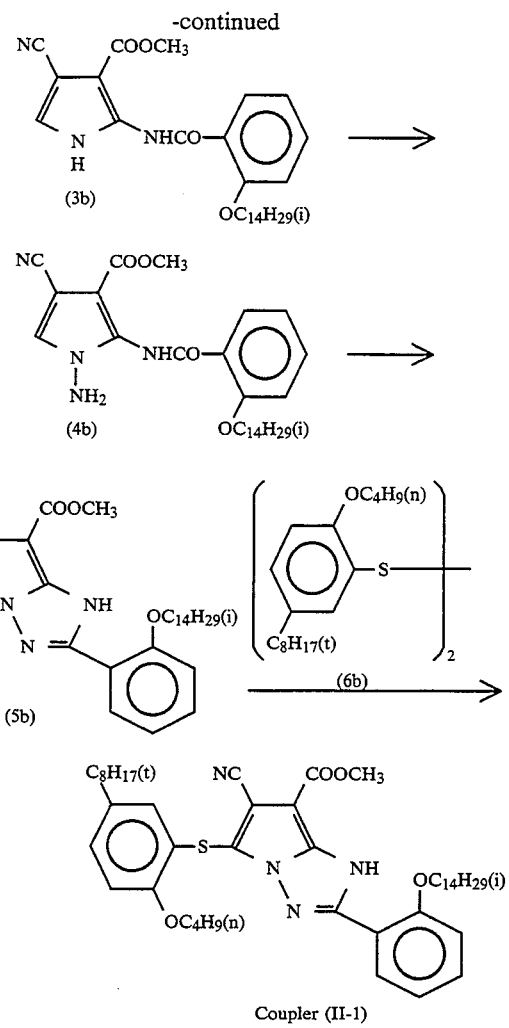

Coupler (II-1)

O-(2-hexyldecyloxy)benzoyl chloride in the amount of 140.8 g (0.4 mol) was added to 300 ml of a dimethylacetamide solution of 66.0 g (0.4 mol) of 2-amino-4-cyano-3-methoxycarbonylpyrrole (1b) at room temperature and stirred for 30 minutes. Water was added to the reaction system, which was then extracted two times, each time with ethyl acetate. The organic layers were combined, washed with water and a saturated saline solution, and dried with anhydrous sodium sulfate. The solvent was removed from the layers by distillation under reduced pressure and the resulting residue was recrystallized from 500 ml of acetonitrile to give 152.3 g (74%) of compound (3b).

A powder of 168.0 g (3.0 mol) of potassium hydroxide was added to 200 ml of dimethylformamide solution of 103.4 g (0.2 mol) of compound (3b) at room temperature and well stirred. During cooling with water, 158.2 g (1.4 mot) of hydroxylamine-O-sulfonic acid was added little by little to the reaction mixture with caution that the temperature did not rise rapidly. After addition, the system was stirred for 30 minutes. An aqueous 0.1N hydrochloric acid solution was dropwise added to this, which was thus neutralized under observation with a pH test paper. This was extracted three times, each time with ethyl acetate, and the organic layer thus separated was washed with water and a saturated saline solution and then dried with anhydrous sodium sulfate. The solvent was removed from this by distillation under reduced pressure, and the resulting residue was purified by column chromatography (with a developing solvent of hexane/ethyl acetate=1/1) to give 6.38 g (6%) of compound (4b).

Five cc of carbon tetrachloride was added to 50 ml of an acetonitrile solution of 5.32 g (10 mmol) of compound (4b) at room temperature, and subsequently 2.88 g (11 mmol) of triphenylphosphine was added thereto and heated under reflux for 8 hours. After being cooled, water was added to the reaction system, which was then extracted three times, each time with ethyl acetate. The organic layer thus separated was washed with water and a saturated saline solution and dried with anhydrous sodium sulfate. The solvent was removed from the layer by distillation under reduced pressure and then the resulting residue was purified by silica gel column chromatography (with a developing solvent of hexane/ethyl acetate=4/1) to give 0.52 g (10%) of compound (5b).

Sulfuryl chloride in the amount of 0.35 cc (4.4 mmol) was added to 10 ml of a methylene chloride solution of 1.17 g (2.00 mmol) of compound (6b) at 0° C. and stirred for one hour. The solvent was removed from the reaction system by distillation under reduced pressure, and 10 ml of methylene chloride was added to the residue. The resulting solution was added to 20 ml of a dimethylformamide solution of 2.06 g (4.4 mmol) of compound (5b) at room temperature and stirred for 30 minutes.

Water was added to the reaction system, which was then extracted three times, each time with ethyl acetate. The organic layer thus separated was washed with water and a saturated saline solution and dried with anhydrous sodium sulfate. The solvent was removed from the layer by distillation under reduced pressure and then the resulting residue was purified by silica gel column chromatography (with a developing solvent of hexane/ethyl acetate=3/1) to give 2.19 g (68%) of the intended Coupler (II-1).

PRODUCTION EXAMPLE 3

Production of Compound (III-1)

Compound (III-1) was produced in accordance with the following reaction route:

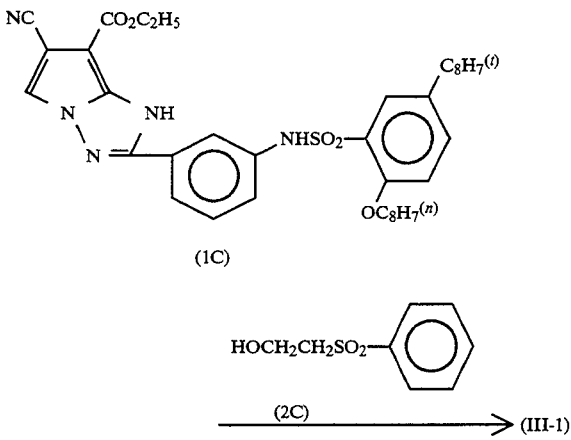

Compound (1c) in the amount of 3.90 g, 18.6 g of compound (2c) and titanium isopropoxide were stirred at 160° C. for 3 hours and 20 minutes. The reaction liquid was poured into ice, and ethyl acetate was added thereto and stirred. This was filtered two times, each time with Celite. The ethyl acetate layer was separated and dried, and then ethyl acetate was removed therefrom by distillation under reduced pressure. Thus, 19.9 g of a brown oily product was obtained. This was purified by silica gel column chromatography (Hex-/EtoAc=2/1) to give 2.12 g of the intended Coupler (III-1).

PRODUCTION EXAMPLE 4

Production of Coupler (III-3)

Coupler (III-3) was produced in accordance with the following reaction route:

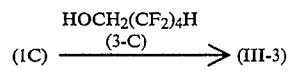

$$(1C) \xrightarrow[\text{(3-C)}]{HOCH_2(CF_2)_4H} (III-3)$$

Compound (1c) in the amount of 3.0 g, 10.2 g of compound (3c) and 0.63 g of titanium isopropoxide were dissolved in 10 ml of sulforane and stirred at 150° C. for 6 hours. Compound (3c) and sulforane were removed from the reaction liquid by distillation under reduced pressure, and the residue was extracted three times, each time with ethyl acetate. This was dried, and ethyl acetate was removed therefrom by distillation under reduced pressure. The residue was then purified by column chromatography to obtain 0.73 g of the intended Coupler (III-3).

The other compounds of the present invention were produced by the same methods as mentioned above.

The photographic material of the present invention may be one which has at least one layer containing the cyan coupler(s) of the present invention on a support. The layer of containing the cyan coupler(s) of the present invention may be a hydrophilic colloid layer on a support. An ordinary photographic material has at least one blue-sensitive silver halide emulsion layer, at least one green-sensitive silver halide emulsion layer and at least one red-sensitive silver halide emulsion layer on a support in this order, though the order of the constitutive layers on the support may be different. The material may contain an infrared-sensitive silver halide emulsion layer in place of at least one of the above-mentioned light-sensitive emulsion layers. These light-sensitive emulsion layers each may comprise a silver halide emulsion having a sensitivity to a respective wavelength range and a color coupler capable of forming a dye having a complementary color to the light to which the emulsion is sensitive, whereby color reproduction by subtractive color photography may be effected. The relationship between the light-sensitive emulsion layer and the color hue of the dye to be formed from the color coupler in the layer is not limited to the above-mentioned constitution, but may be of any other relationship.

Where the cyan couplers of the present invention are applied to photographic materials, they are preferably incorporated into the red-sensitive silver halide emulsion layer of the material.

The content of the cyan coupler(s) of the present invention in the photographic material may be from $1 \times 10^{-3}$ mol to 1 mol, preferably from $2 \times 10^{-3}$ mol to $3 \times 10^{-1}$ mol, per mol of silver halide.

The cyan couplers of the present invention can be introduced into the photographic material by various known methods. Preferred is an oil-in-water dispersion method in which the coupler is dissolved in a high boiling point organic solvent (if desired, along with a low boiling point organic solvent) and the resulting solution is dispersed in an aqueous gelatin solution by emulsification and added to a silver halide emulsion.

Examples of the high boiling point solvents to be used in an oil-in-water dispersion method which may be employed in the present invention are described in U.S. Pat. No. 2,322,027. One polymer dispersion method suitable for the present invention is a latex dispersion method which may also be employed in the present invention. The process of such a latex dispersion method, its effect, and specific examples of the latexes for impregnation to be used in the method, are described in U.S. Pat. No. 4,199,363, German Patent OLS Nos. 2,541,274 and 2,541,230, JP-B 53-41091 and European Patent Laid-Open No. 029104. A dispersion method using organic solvent-soluble polymers may also be employed in the present invention, which is described in PCT Laid-Open WO88/00723.

Examples of high boiling point organic solvents suitable for the above-mentioned oil-in-water method include phthalates (e.g., dibutyl phthalate, dioctyl phthalate, dicyclohexyl phthalate, di-2-ethylhexyl phthalate, decyl pnthalate, bis(2,4-di-t-amylphenyl) isophthalate, bis(1,1-diehtylpropyl phthalate), phosphates or phosphonates (e.g., diphenyl phosphate, triphenyl phosphate, tricresyl phosphate, 2-ethylhexyl-diphenyl phosphate, dioctylbutyl phosphate, tricyclohexyl phosphate, tri-2-ethylhexyl phosphate, tridodecyl phosphate, di-2-ethylhexylphenyl phosphonate), benzoates (e.g., 2-ethylhexyl benzoate, 2,4-dichlorobenzoate, dodecyl benzoate, 2-ethylhexyl p-hydroxybenzoate), amides (e.g., N,N-diethyldodecanamide, N,N-diethyllaurylamide), alcohols or phenols (e.g., isostearyl alcohol, 2,4-di-tert-amylphenol), aliphatic esters (e.g., dibutoxyethyl succinate, di-2-ethylhexyl succinate, 2-hexyldecyl tetradecanoate, tributyl citrate, diethyl azelate, isostearyl lactate, trioctyl citrate), aniline derivatives (e.g., N,N-dibutyl-2-butoxy-5-tertoctylaniline), chlorinated paraffins (e.g., paraffins having chlorine a content of from 10% to 80%), trimesates (e.g., tributyl trimesate), dodecylbenzene, diisopropylnaphthalene, phenols (e.g., 2,4-di-tert-amylphenol, 4-dodecyloxyphenol, 4-dodecyloxycarbonylphenol 4-(4-dodecyloxyphenylsulfonyl)-phenol), carboxylic acids (e.g., 2-(2,4-di-tert-amylphenoxybutyric acid, 2-ethoxyoctanedecanoic acid), and alkylphosphoric acids (e.g., di-(2-ethylhexyl)phosphoric acid, diphenylphosphoric acid). The auxiliary solvents suitable to be used with the high boiling point organic solvents include, for example, organic solvents having a boiling point of approximately from 30° C. to 160° C., such as ethyl acetate, butyl acetate, ethyl propionate, methyl ethyl ketone, cyclohexanone, 2-ethoxyethyl acetate, and dimethylformamide.

The proportion by weight of the high boiling point organic solvent to be used in the case may be from 0 to 10.0 times, preferably from 0 to 4.0 times, the amount of the coupler.

As the silver halide emulsions and other elements (e.g., additives, etc.) constituting the photographic material of the present invention, the photographic layers constituting the material (e.g., arrangement of layers), and the methods of processing the material, and the additives suitable in the processing methods, those described in the following patent publications, especially in European Patent 0,355,660A2, are preferably employed.

| Photographic Elements | JP-A 62-215272 | JP-A 2-33144 | EP 0,355,660A2 |
|---|---|---|---|
| Silver Halide Emulsions | From page 10, right upper column, line 6 to page 12, left lower column, line 5; and from page 12, right lower column, line 4 to page 13, left upper column, line 17 | From page 28, right upper column, line 16 to page 29, right lower column, line 11; and page 30, lines 2 to 5 | From page 45, line 53 to page 47, line 3; and page 47, lines 20 to 22 |
| Silver Halide Solvents | Page 12, left lower column, lines 6 to 14; and from page 13, left upper column, line 3 from below to page 18, left lower column, last line | — | — |
| Chemical Sensitizers | Page 12, from left lower column, line 3 from below to right lower column, line 5 from below; and from page 18, right lower column, line 1 to page 22, right upper column, line 9 from the bottom | Page 29, right lower column, line 12 to last line | Page 47, lines 4 to 9 |
| Color Sensitizers (Color Sensitizing Methods) | From page 22, right upper column, line 8 from below to page 38, last line | Page 30, left upper column, lines 1 to 13 | Page 47, lines 10 to 15 |
| Emulsion Stabilizers | From page 39, left upper column, line 1 to page 72, right upper column, last line | Page 30, from left upper column, line 14 to right upper column, line 1 | Page 47, lines 16 to 19 |
| Development Promoters | From page 72, left lower column, line 1 to page 91, right upper column, line 3 | — | — |
| Color Couplers (Cyan, | From page 91, right | From page 3, right | Page 4, lines 15 to |

-continued

| Photographic Elements | JP-A 62-215272 | JP-A 2-33144 | EP 0,355,660A2 |
|---|---|---|---|
| Magenta and Yellow Couplers) | upper column, line 4 to page 121, left upper column, line 6 | upper column, line 14 to page 18, left upper column, last line; and from page 30, right upper column, line 6 to page 35, right lower column, line 11 | 27; from page 5, line 30 to page 8, last line; page 45, lines 29 to 31; and from page 47, line 23 to page 63, line 50 |
| Coloring Enhancers | From page 121, left upper column, line 7 to page 125, right upper column, line 1 | — | — |
| Ultraviolet Absorbents | From page 125, right upper column, line 2 to page 127, left lower column, last line | From page 37, right lower column, line 14 to page 38, left upper column, line 11 | Page 65, lines 22 to 31 |
| Anti-fading Agents (Color Image Stabilizers) | From page 127, right lower column, line 1 to page 137, left lower column, line 8 | From page 36, right upper column, line 12 to page 37, left upper column, line 19 | From page 4, line 30 to page 5, line 23; from page 29, line 1 to page 45, line 25; page 45, lines 33 to 40; and page 65, lines 2 to 21 |
| High Boiling Point and/or Low Boiling Point Organic Solvents | From page 137, left lower column, line 9 to page 144, right upper column, last line | From page 35, right lower column, line 14 to page 36, left upper column, line 4 from the bottom | Page 64, lines 1 to 51 |
| Dispersing Methods of Photographic Additives | From page 144, left lower column, line 1 to page 146, right upper column, line 7 | From page 27, right lower column, line 10 to page 128, left upper column, last line; and from page 35, right lower column, line 12, to page 36, right upper column, line 7 | From page 63, line 51 to page 64, line 56 |
| Hardening Agents | From page 146, right upper column, line 8 to page 155, left lower column, line 4 | — | — |
| Developing Agent Precursors | Page 155, from left lower column, line 5 to right lower column, line 2 | — | — |
| Development Inhibitor Releasing Compounds | Page 155, right lower column, lines 3 to 9 | — | — |
| Supports | From page 155, right lower column, line 19 to page 156, left upper column, line 14 | From page 38, right upper column, line 18 to page 39, left upper column, line 3 | From page 66, line 29 to page 67, line 13 |
| Constitution of the Photographic Layers | Page 156, from left upper column, line 15 to right lower column, line 14 | Page 28, right upper column, lines 1 to 15 | Page 45, lines 41 to 52 |
| Dyes | From page 156, right lower column, line 15 to page 184, right lower column, last line | Page 38, from left upper column, line 12 to right upper column, line 7 | Page 66, lines 18 to 22 |
| Color Mixing Preventing Agents | From page 185, left upper column, line 1 to page 188, right lower column, line 3 | Page 36, right lower column, lines 8 to 11 | From page 64, line 57 to page 65, line 1 |
| Gradation Adjusting Agents | Page 188, right lower column, lines 4 to 8 | — | — |
| Stain Inhibitors | From page 188, right lower column, line 9 to page 193, right lower column, line 10 | Page 37, from left upper column, last line to right lower column, line 13 | From page 65, line 32 to page 66, line 17 |
| Surfactants | From page 201, left lower column, line 1 to page 210, right upper column, last one | From page 18, right upper column, line 1 to page 24, right lower column, last line; and page 27, from left lower column, line 10 from below to right lower column, line 9 | — |
| Fluorine-Containing Compounds (such as antistatic agents, | From page 210, left lower column, line 1 to page 222, left | From page 25, left upper column, line 1 to page 27, right | — |

-continued

| Photographic Elements | JP-A 62-215272 | JP-A 2-33144 | EP 0,355,660A2 |
|---|---|---|---|
| coating aids, lubricants, and anti-blocking agents) | lower column, line 5 | lower column, line 9 | |
| Binders (hydrophilic colloids) | From page 222, left lower column, line 6 to page 225, left upper column, last line | Page 38, right upper column, lines 8 to 18 | Page 66, lines 23 to 28 |
| Tackifiers | From page 225, right upper column, line 1 to page 227, right upper column, line 2 | — | — |
| Antistatic Agents | From page 227, right upper column, line 3 to page 230, left upper column, line 1 | — | — |
| Polymer Latexes | From page 230, left upper column, line 2 to page 239, last line | — | — |
| Mat Agents | Page 240, from left upper column, line 1 to right upper column, last line | — | — |
| Photographic Processing Methods (Processing steps and additives) | From page 3, right upper column, line 7 to page 10, right upper column, line 5 | From page 39, left upper column, line 4 to page 42, left upper column, last line | From page 67, line 14 to page 69, line 28 |

The cited specification of JP-A 62-215272 is the one as amended by the letter of amendment filed on March 16, 1987.
Of the above-mentioned color couplers, the so-called shortwave type yellow couplers described in JP-A 63-231451, 63-123047, 63-241547, 1-173499, 1-213648 and 1-250944 are also preferably used as the yellow couplers.

The silver halides constituting the photographic material of the present invention include silver chloride, silver bromide, silver chlorobromide, silver iodochlorobromide and silver iodobromide. For the purpose of rapidly processing the photographic material, preferred is a silver chlorobromide emulsion having a silver chloride content of 90 mol % or more, preferably 95% or more, especially preferably 98% or more, or a pure silver chloride emulsion, which does not substantially contain silver iodide.

For the purpose of improving the sharpness of the image to be formed on the photographic material of the present invention, it is preferred to incorporate a dye capable of being decolored by photographic processing, as described in European Patent 0,337,490A2 (especially oxonole dyes), into the hydrophilic colloid layer of the material in an amount such that the optical reflection density of the material at 680 mm may be 0.70 or more, or to incorporate a titanium oxide which has been surface-treated with a di-hydric to tetra-hydric alcohol (e.g., trimethylolethane) into the water-proof resin layer of the support of the material in an amount of 12% by weight or more, more preferably 14% by weight or more.

The photographic material of the present invention preferably contains a color image preservability improving compound, for example, the one described in European Patent 0,277,589A2, along with the couplers. Incorporation of such a color image preservability improving compound into the material along with a pyrazoloazole magenta coupler is preferred.

To eliminate side effects, such as, for example, the generation of stain due to the reaction of a color developing agent or an oxidation product thereof remaining in a layer during storage after processing, it is preferable to use compounds (A) of EP 0,277,589A2 which chemically combine with an aromatic amine type developing agent remaining after a color development processing to form a chemically inactive and substantially colorless compound, and/or compounds (B) of EP 0,277,589A2 which chemically combine with the oxidation product of an aromatic amine type developing agent remaining after a color development processing to form a chemically inactive and substantially colorless compound.

The photographic material of the present invention also preferably contains a microbicide, such as the one described in JP-A 63-271247, for the purpose of preventing the propagation of various fungi and bacteria in the hydrophilic colloid layer of the processed material which would deteriorate the image formed on the material.

As a support in the photographic material of the present invention, a white polyester support or a support having a white pigment-containing layer on the side facing the silver halide emulsion layers coated thereover, may be employed for displays. In order to improve the sharpness of the image to be formed, it is preferred to provide an anti-halation layer on the support, either on the side facing the silver halide emulsion layers coated thereover or on the opposite back side thereto. In particular, it is preferred that the transmission density of the support fall within the range of from 0.35 to 0.8, in order that the display with the photographic material of the present invention be may seen with either a reflecting light or a transmitting light.

The photographic material of the present invention may be exposed either with visible rays or with infrared rays. For exposure of the material, either a low intensity exposure or a high intensity short-time exposure may be employed. In particular, in the latter case, a laser scanning exposure system is preferred where the exposure time is shorter than $10^{-4}$ second per pixel.

During the exposure of the photographic material of the present invention, a band stop filter described in U.S. Pat. No. 4,880,726 is preferably used. Using it, rays of causing color mixture may be removed so that the color reproducibility of the exposed material is improved noticeably.

Next, the present invention will be explained in more detail by way of the following examples, which, however, are not intended to restrict the scope of the present invention.

EXAMPLE 1

Formation of Photographic Material Sample No. 101

Two layers, each having the composition mentioned below, were coated on a cellulose triacetate film base to form a photographic material Sample No. 101. The coating liquid for the first layer was prepared in the manner mentioned below.

Preparation of Coating Liquid for First Layer

Cyan coupler (E×C) in the amount of 1.01 g and 1.0 g of dibutyl phthalate were completely dissolved in 10.0 cc of ethyl acetate. The coupler solution in ethyl acetate was added to 42 g of an aqueous 10% gelatin solution (containing 5 g/liter of sodium dodecylbenzenesulfonate) and emulsified and dispersed with a homogenizer. After emulsification and dispersion, distilled water was added to the dispersion to make it 100 g as a whole. One hundred g of the emulsified dispersion and 8.2 g of a red-sensitive high-silver chloride emulsion (with a silver bromide content of 0.5 mol %, to which $1.0 \times 10^{-4}$ mol per mol of silver halide of the following red-sensitizing Dye E was added) were blended to prepare a coating liquid for the first layer having the composition mentioned below.

As a gelatin hardening agent, 1-hydroxy-3, 5-dichloro-s-triazine sodium salt was used.

Cyan coupler (ExC)

[Chemical structure diagram]

Sensitizing Dye E for Red-sensitive Emulsion

[Chemical structure diagram]

Layer Constitution

The layer constitution of the sample is shown below.
Support:
Cellulose Triacetate Film
First Layer: Emulsion Layer

| | |
|---|---|
| Red-Sensitive High-Silver Chloride Emulsion | 0.86 g/m² as Ag |
| Gelatin | 2.50 g/m² |
| Cyan Coupler (ExC) | 0.49 g/m² |
| Tricresyl Phosphate | 1.00 g/m² |

Second Layer: Protective Layer

| | |
|---|---|
| Gelatin | 1.60 g/m² |

Formation of Photographic Material Sample Nos. 102 to 115

Sample Nos. 102 to 115 were formed in the same manner as in formation of Sample No. 101, except that cyan coupler (ExC) was replaced in the same molar amount by the coupler as indicated in Table A below.

Sample Nos. 101 to 115 thus prepared were subjected to continuous wedgewise exposure with a white light and then developed in accordance with the process mentioned below.

The density of each of the thus processed samples was measured, whereupon the absorption spectrum in the high density area was measured. On the absorption spectrum thus measured, the absorbency value in the associated condition was obtained on the basis of the absorbency of the non-associated condition being 1.0. The value obtained is shown in Table A. The larger the value, the more the spectrum of the associated condition becomes to indicate unfavorable color reproduction.

Development Process:

Rinsing was effected by a countercurrent system from rinsing tank (3) to rinsing tank (1).

The compositions of the processing solutions used are mentioned below:

Color Developer

| | |
|---|---|
| Water | 800 ml |
| Ethylenediamine-N,N,N,N-tetramethylenephosphonic Acid | 3.0 g |
| Triethanolamine | 8.0 g |
| Potassium Chloride | 3.1 g |
| Potassium Bromide | 0.015 g |
| Potassium Carbonate | 25 g |
| Hydrazinodiacetic Acid | 5.0 g |
| N-ethyl-N-(β-methanesulfonamidoethyl)-3-methyl-4-aminoaniline Sulfate | 5.0 g |
| Brightening Agent (WHITEX-4, produced by Sumitomo Chemical Co.) | 2.0 g |
| Water to make | 1000 ml |
| pH (with potassium hydroxide) | 10.05 |

| | |
|---|---|
| Water | 400 ml |
| Ammonium Thiosulfate Solution (700 g/liter) | 100 ml |
| Ammonium Sulfite | 45 g |
| Ammonium Ethylenediaminetetraacetate/Fe(III) | 55 g |
| Ethylenediaminetetraacetic Acid | 3 g |
| Ammonium Bromide | 30 g |
| Nitric Acid (67%) | 27 g |
| Water to make | 1000 ml |
| pH | 5.8 |

Rinsing Solution

Ion-exchanged Water (having calcium content and magnesium content of each being 3 ppm).

| Processing Step | Temperature | Time |
|---|---|---|
| Color Development | 38° C. | 45 sec |
| Bleach-fixation | 35° C. | 45 sec |

-continued

| Processing Step | Temperature | Time |
|---|---|---|
| Rinsing (1) | 35° C. | 30 sec |
| Rinsing (2) | 35° C. | 30 sec |
| Rinsing (3) | 35° C. | 30 sec |
| Drying | 80° C. | 60 sec |

TABLE A

| Sample No. | Coupler | Absorbency in Associated Condition | Remarks |
|---|---|---|---|
| 101 | ExC | 2.30 | comparative sample |
| 102 | (I-7) | 0.94 | sample of the invention |
| 103 | (I-8) | 1.25 | sample of the invention |
| 104 | (I-12) | 0.55 | sample of the invention |
| 105 | (I-4) | 0.90 | sample of the invention |
| 106 | (I-21) | 0.23 | sample of the invention |
| 107 | (II-1) | 0.85 | sample of the invention |
| 108 | (II-4) | 0.96 | sample of the invention |
| 109 | (II-9) | 0.21 | sample of the invention |
| 110 | (II-11) | 0.25 | sample of the invention |
| 111 | (II-14) | 0.53 | sample of the invention |
| 112 | (I-24) | No associated peak | " |
| 113 | (II-30) | " | " |
| 114 | (II-31) | " | " |
| 115 | (II-35) | " | " |

From Table A above, it is understood that the couplers of the present invention give hardly any unnecessary spectrum of an associated condition and are therefore more advantageous for color reproduction than the comparative coupler.

The developed Samples Nos. 102 to 106 were stored under the condition of 80° C. and 70% RH for 3 days for a forced aging test, whereupon all the samples showed no reduction in density. From this, the dyes formed in the respective samples were identified to be excellent in the fastness.

EXAMPLE 2

Formation of Sample No. 201

Sample No. 201 was prepared in the same manner as Sample No. 101 in Example 1, except that the red-sensitive high-silver chloride emulsion in the first layer was changed to 4.1 g (having a silver bromide content of 0.6%, to which $1.2 \times 10^{-4}$ mol per mol of silver halide of the red-sensitizing dye was added) and that the constitution of the first layer was changed to the following:

First Layer: Emulsion Layer

| Red-Sensitive High-Silver Chloride Emulsion | 0.42 g/m² as Ag |
|---|---|
| Gelatin | 1.80 |
| Cyan Coupler (ExC) | 0.30 |
| Tricresyl Phosphate | 0.72 |

Formation of Samples Nos. 202 to 214

Sample Nos. 202 to 214 were prepared in the same manner as in preparation of Sample No. 201, except that the cyan coupler (ExC) was replaced by the same molar amount of the coupler as indicated in Table B below. Cyan coupler (ExC-2) is as follows:

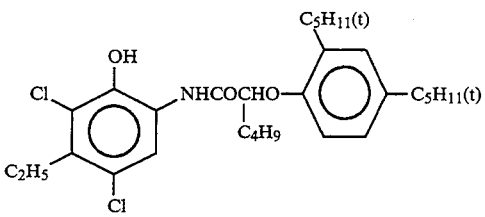

Samples Nos. 201 to 210 thus prepared were subjected to continuous wedgewise exposure with a white light and the processed in the same manner as in Example 1 except that the color development time was shortened to 30 seconds (short-time development).

The density of each of the processed samples was measured through a red filter to give a sensitometry line. From this, the fog density (Dmin) and the maximum color density (Dmax) were read out and shown in Table B below.

TABLE B

| Sample No. | Coupler | Dmin | Dmax | Remarks |
|---|---|---|---|---|
| 201 | ExC | 0.13 | 1.84 | comparative sample |
| 202 | ExC-2 | 0.05 | 1.32 | comparative sample |
| 203 | (III-1) | 0.04 | 2.24 | sample of the invention |
| 204 | (III-3) | 0.04 | 2.19 | sample of the invention |
| 205 | (III-5) | 0.05 | 2.14 | sample of the invention |
| 206 | (III-9) | 0.05 | 2.11 | sample of the invention |
| 207 | (III-15) | 0.06 | 2.20 | sample of the invention |
| 208 | (III-25) | 0.05 | 2.18 | sample of the invention |
| 209 | (III-2) | 0.06 | 2.02 | sample of the invention |
| 210 | (III-19) | 0.05 | 0.95 | sample of the invention |
| 211 | (I-24) | 0.05 | 1.50 | sample of the invention |
| 212 | (II-30) | 0.04 | 1.70 | sample of the invention |
| 213 | (II-31) | 0.05 | 1.75 | sample of the invention |
| 214 | (II-35) | 0.05 | 1.80 | sample of the invention |

From Table B above, it is understood that Sample Nos. 203 to 214, each containing a coupler of the present invention had a higher color density than the Comparative Sample No. 202. In addition, it was visually observed that the former each had a clear color and a higher transparency than the latter, and it was also confirmed that the former were superior to the latter in point of color hue by spectral measurement. Although comparative Sample No. 201 had an excellent color hue, the fog density thereof was noticeably high. On the other hand, it is understood that the couplers of the present invention each gave a low fog value and a high color density.

The developed Sample Nos. 201 to 210 were stored under the conditions of 80° C. and 70% RH for 3 days for a forced aging test, whereupon the color density of Sample Nos. 203 to 210 each containing the coupler of the present invention did not lower. From this, it was determined that the dyes obtained from the couplers of the present invention were highly fast.

EXAMPLE 3

A paper support, both surfaces of which had been laminated with polyethylene, was subjected to corona discharging treatment, and a gelatin subbing layer containing sodium dodecylbenzenesulfonate was provided thereon. Next, several photographic constitutive layers each having the composition mentioned below were coated thereover to form a multi-layer color photographic material (Sample No. 301). The coating liquids were prepared in the manner mentioned below.

Preparation of Coating Liquid for First Layer

Yellow coupler (ExY) in the amount of 153.0 g, 15.0 g of color image stabilizer (Cpd-1), 7.5 g of color image stabilizer (Cpd-2) and 16.0 g of color image stabilizer (Cpd-3) were dissolved in 25 g of solvent (Solv-1), 25 g of solvent (Solv-2) and 180 cc of ethyl acetate. The resulting solution was dispersed by emulsification in 1000 g of an aqueous 10% gelatin solution containing 60 cc of 10% sodium dodecylbenzenesulfonate and 10 g of citric acid to obtain an emulsified Dispersion A. Separately, a silver chlorobromide Emulsion A (3/7 (by mol of silver) mixture of large-size Emulsion A of cubic grains with a mean grain size of 0.88 μm and small-size Emulsion A of cubic grains with a mean grain size of 0.70 μm; the fluctuation coefficient of the grain size distribution of the two emulsions was 0.08 and 0.10, respectively; both emulsions had a 0.3 mol % silver bromide local phase on a part of the grain surface) was prepared. The emulsion contained the following blue-sensitizing Dyes A and B each in an amount of $2.0 \times 10^{-4}$ mol per mol of silver in the large-size Emulsion A and $2.5 \times 10^{-4}$ mol per mol of silver in the small-size Emulsion A. Chemical ripening of the emulsion was effected by sulfur sensitization and gold sensitization. The emulsified Dispersion A as previously prepared and the silver chlorobromide Emulsion A were blended to give a coating liquid for the first layer having the composition mentioned below.

Preparation of Coating Liquid for Fifty Layer

Sixty cc of ethyl acetate was added to 33.0 g of cyan coupler (ExC-1), 18.0 g of ultraviolet absorbent (UV2), 30.0 g of color image stabilizer (Cpd-1), 15.0 g of color image stabilizer (Cpd-9), 15.0 g of color image stabilizer (Cpd-10), 1.0 g of color image stabilizer (Cpd-11), 1.0 g of color image stabilizer (Cpd-8), 1.0 g of color image stabilizer (Cpd-6), 22.0 g of solvent (Solv-6) and 1.0 g of solvent (Solv-1) and dissolved. The resulting solution was added to 500 cc of an aqueous 20% gelatin solution containing 8 cc of sodium dodecylbenzenesulfonate and then emulsified and dispersed with an ultrasonic homogenizer to prepare an emulsified Dispersion C. Separately, a silver chlorobromide Emulsion C (a ¼ (by mol of silver) mixture of large-size Emulsion C of cubic grains with a mean grain size of 0.50 μm and small-size Emulsion C of cubic grains with a mean grain size of 0.41 μm; the fluctuation coefficient of the grain size distribution of the two emulsions was 0.09 and 0.11, respectively; both emulsions had a 0.8 mol % of silver bromide local phase on a part of the grain surface) was prepared. The emulsion contained the following red-sensitizing Dye E in an amount of $0.9 \times 10^{-4}$ mol per mol of silver in the large-size Emulsion C and $1.1 \times 10^{-4}$ mol per mol of silver in the small-size Emulsion C. Further, it contained Compound F in an amount of $2.6 \times 10^{-3}$ mol per mol of silver halide. Chemical ripening of Emulsion C was effected by sulfur sensitization and gold sensitization. The emulsified Dispersion C as previously prepared and the red-sensitive silver chlorobromide Emulsion C were blended to give a coating liquid for the fifth layer having the composition mentioned below.

The coating liquids for the second layer, third layer, fourth layer, sixth layer and seventh layer were also prepared in the same manner as in preparation of the coating liquid for the first layer. As a gelatin hardening agent for each layer, added thereto was 1-hydroxy-3,5-dichloro-s-triazine sodium salt.

The respective layers contained 25.0 mg/m² as a whole, of Cpd-14 and 50 mg/m², as a whole, of Cpd-15.

Color sensitizing dyes added to the silver chlorobromide emulsions of the respective light-sensitive emulsion layers are shown below.

Blue-sensitive Emulsion Layer

Sensitizing Dye A

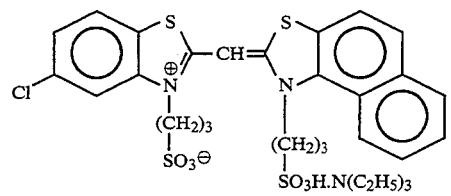

Sensitizing Dye B

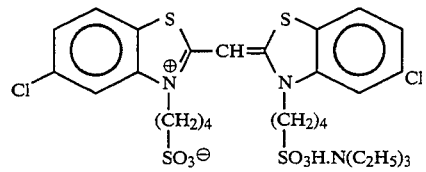

Green-sensitive Emsulsion Layer

Sensitizing Dye C

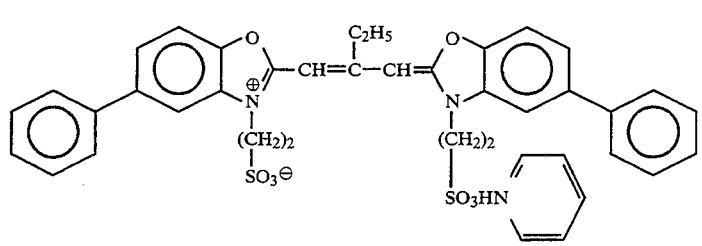

($4.0\times10^{-4}$ mol per mol of silver halide to large-size Emulsion B; and $5.6\times10^{-4}$ mol per mol of silver halide to small-size Emulsion B)

Sensitizing Dye D

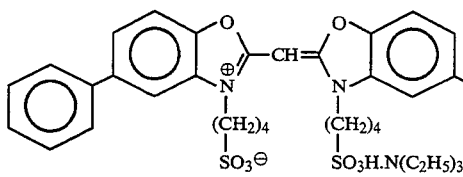

($7.0\times10^{-5}$ mol per mol of silver halide to large-size Emulsion B; and $1.0\times10^{-5}$ mol per mol of silver halide to small-size Emulsion B)

Red-sensitive Emsulsion Layer

Sensitizing Dye E

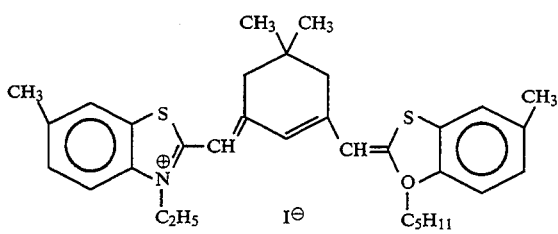

Compound F

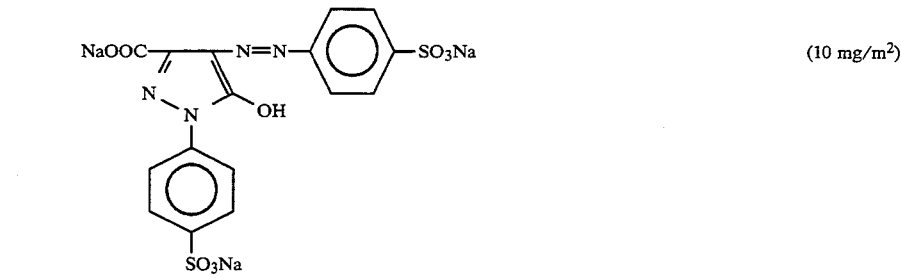

To the blue-sensitive emulsion layer, green-sensitive emulsion layer and red-sensitive emulsion layer was added 1-(5-methylureidophenyl)-5-mercaptotetrazole, in an amount of $8.5\times10^{-5}$ mol, $7.7\times10^{-4}$ mol and $2.5\times10^{-4}$ mol, per mol of silver halide, respectively.

To the blue-sensitive emulsion layer and green-sensitive emulsion layer was added 4-hydroxy-6-methyl-1,3,3a,7-tetrazaindene in an amount of $1\times10^{-4}$ mol and $2\times10^{-4}$ mol, per mol of silver halide, respectively.

For anti-irradiation, the following dyes were added to the respective emulsion layers, the coated amount being parenthesized.

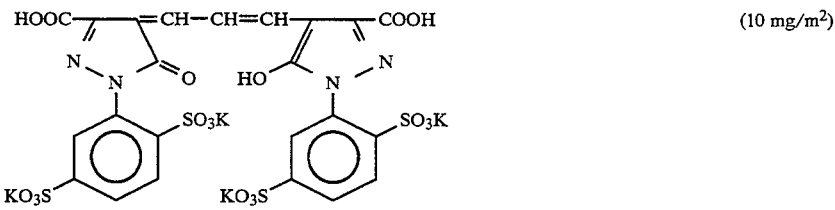 (10 mg/m²)

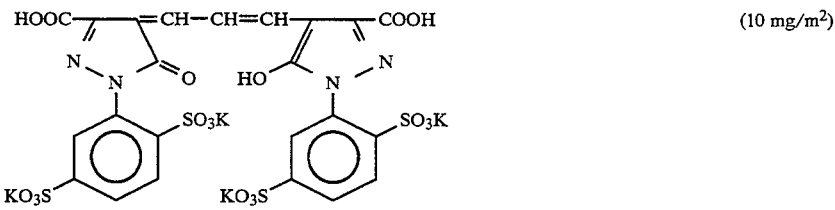 (10 mg/m²)

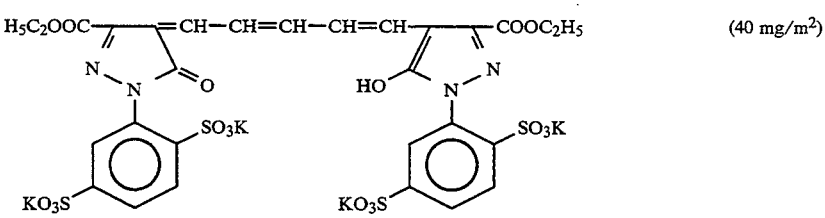 (40 mg/m²)

and

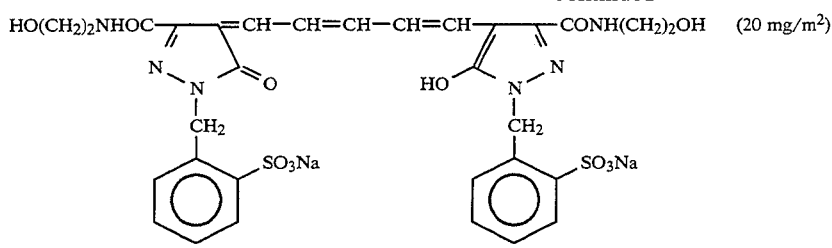

(20 mg/m²)

Layer Constitution:

The compositions of the layers constituting Sample No. 301 are mentioned below, in which the numerical value indicates the amount coated (g/m²) and the amount of the silver halide coated is represented as silver therein.

Support:
Polyethylene-laminated Paper (containing white pigment ($TiO_2$) and bluish dye (ultramarine) in polyethylene below the first layer)

First Layer: Blue-sensitive Emulsion Layer

| | |
|---|---|
| Above-mentioned Silver Chlorobromide Emulsion A | 0.27 |
| Gelatin | 1.36 |
| Yellow Coupler (ExY) | 0.79 |
| Color Image Stabilizer (Cpd-1) | 0.08 |
| Color Image Stabilizer (Cpd-2) | 0.04 |
| Color Image Stabilizer (Cpd-3) | 0.08 |
| Solvent (Solv-1) | 0.13 |
| Solvent (Solv-1) | 0.13 |

Second Layer: Color Mixing Preventing

| | |
|---|---|
| Gelatin | 1.00 |
| Color Mixing Preventing Agent (Cpd-4) | 0.06 |
| Solvent (Solv-7) | 0.03 |
| Solvent (Solv-2) | 0.25 |
| Solvent (Solv-3) | 0.25 |

Third Layer: Green-sensitive Emulsion Layer

| | |
|---|---|
| Silver Chlorobromide Emulsion (a ⅓ mixture (by mol of Ag) of large-size Emulsion B of cubic grains with a mean grain size of 0.55 μm and small-size Emulsion B of cubic grains with a mean grain size of 0.39 μm; the two emulsions had a fluctuation coefficient of the grain size distribution of 0.10 and 0.08, respectively; they contained a 0.8 mol % AgBr local phase on a part of the grain surface) | 0.13 |
| Gelatin | 1.45 |
| Magenta Coupler (ExM) | 0.16 |
| Color Image Stabilizer (Cpd-5) | 0.15 |
| Color Image Stabilizer (Cpd-2) | 0.03 |
| Color Image Stabilizer (Cpd-6) | 0.01 |
| Color Image Stabilizer (Cpd-7) | 0.01 |
| Color Image Stabilizer (Cpd-8) | 0.08 |

| | |
|---|---|
| Solvent (Solv-3) | 0.50 |
| Solvent (Solv-4) | 0.15 |
| Solvent (Solv-5) | 0.15 |

Fourth Layer: Color Mixing Preventing Layer

| | |
|---|---|
| Gelatin | 0.70 |
| Color Mixing Preventing Agent (Cpd-4) | 0.04 |
| Solvent (Solv-7) | 0.02 |
| Solvent (Solv-2) | 0.18 |
| Solvent (Solv-3) | 0.18 |

Fifth Layer: Red-sensitive Emulsion Layer

| | |
|---|---|
| Silver Chlorobromide Emulsion C | 0.20 |
| Gelatin | 0.85 |
| Cyan Coupler (ExC) | 0.33 |
| Ultraviolet Absorbent (UV-2) | 0.18 |
| Color Image Stabilizer (Cpd-1) | 0.30 |
| Color Image Stabilizer (Cpd-9) | 0.15 |
| Color Image Stabilizer (Cpd-10) | 0.15 |
| Color Image Stabilizer (Cpd-11) | 0.01 |
| Solvent (Solv-6) | 0.20 |
| Color Image Stabilizer (Cpd-8) | 0.01 |
| Color Image Stabilizer (Cpd-6) | 0.01 |
| Solvent (Solv-1) | 0.01 |

Sixth Layer: Ultraviolet Absorbing Layer

| | |
|---|---|
| Gelatin | 0.55 |
| Ultraviolet Absorbent (UV-1) | 0.38 |
| Color Image Stabilizer (Cpd-12) | 0.15 |
| Color Image Stabilizer (Cpd-5) | 0.02 |

Seventh Layer: Protective Layer

| | |
|---|---|
| Gelatin | 1.13 |
| Acryl-modified Copolymer of Polyvinyl Alcohol (modification degree 17%) | 0.05 |
| Liquid Paraffin | 0.02 |
| Color Image Stabilizer (Cpd-5) | 0.01 |

Compounds used above are shown below:
(ExY) Yellow Coupler:
1/1 ( by mol ) mixture of:

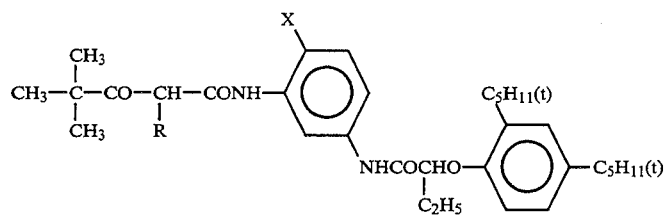

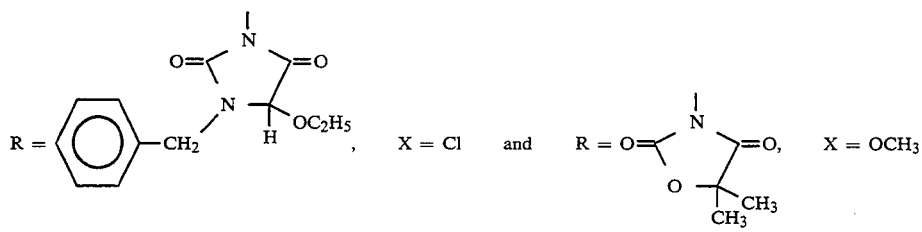, X = Cl and 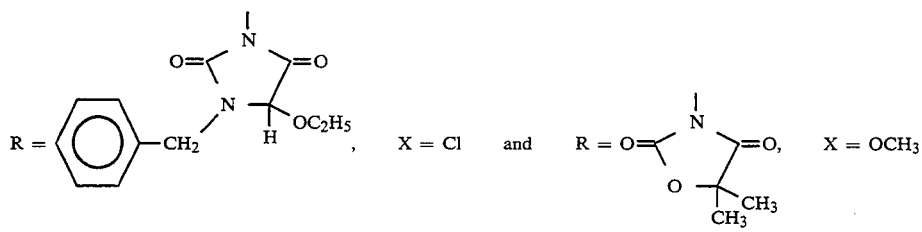, X = OCH₃
(ExM) Magenta Coupler:
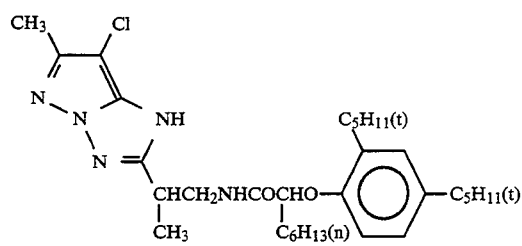
(ExC-1) Cyan Coupler:
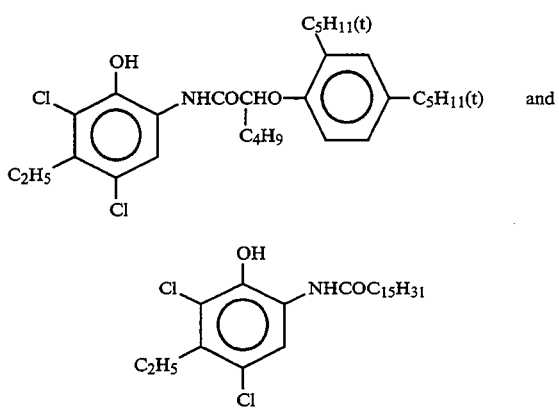
(Cpd-1) Color Image Stabilizer:
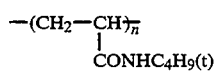
(mean molecular weight: 60,000)
(Cpd-2) Color Image Stabilizer:
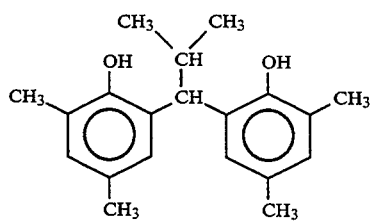
(Cpd-3) Color Image Stabilizer:
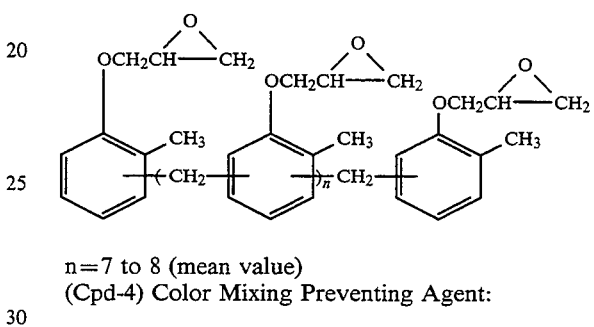
n = 7 to 8 (mean value)
(Cpd-4) Color Mixing Preventing Agent:
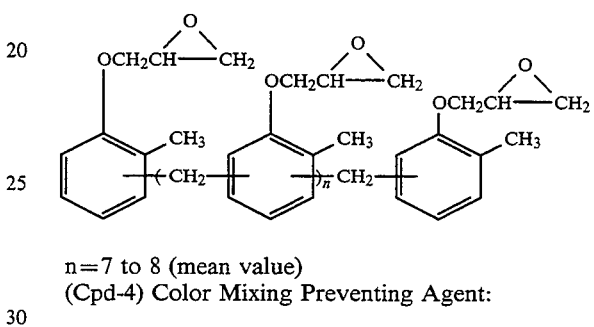
(Cpd-5) Color Image Stabilizer:
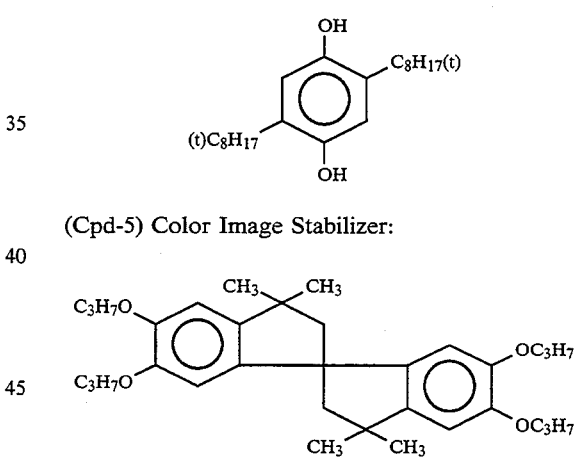
(Cpd-6):
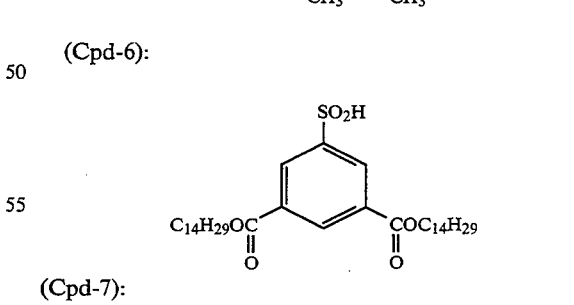
(Cpd-7):
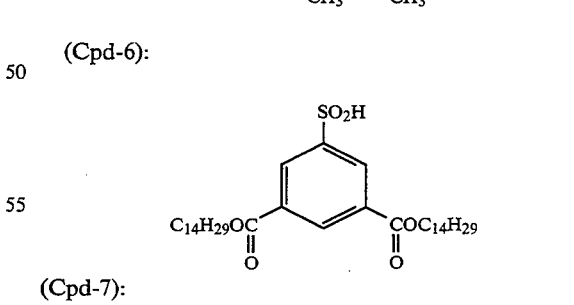
(Cpd-8) Color Image Stabilizer:

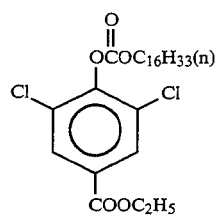
(Cpd-9) Color Image Stabilizer:
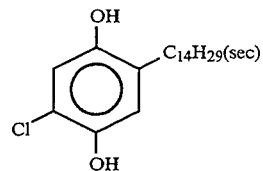
(Cpd-10) Color Image Stabilizer:
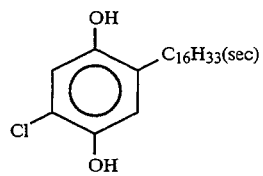
(Cpd-11):
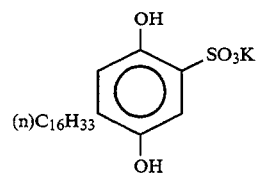
(Cpd-12):
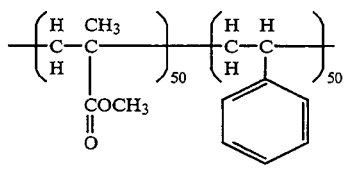
(mean molecular weight: 60,000)
(mean molecular weight: 60,000)
(Cpd-13):
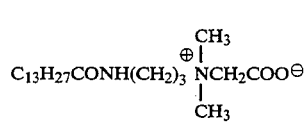
(Cpd-14) Antiseptic:
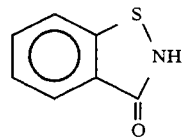
(Cpd-15) Antiseptic:
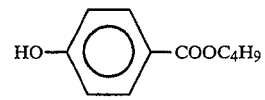
(UV-1) Ultraviolet Absorbent:
10/5/1/5 (by weight) mixture of:
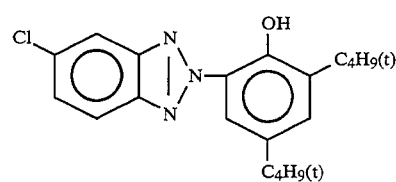
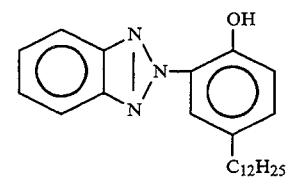
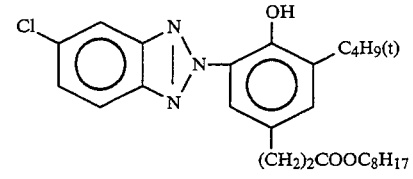
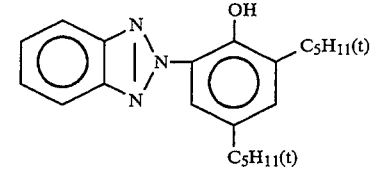
(UV-2) Ultraviolet Absorbent:
1/2/2 (by weight) mixture of:
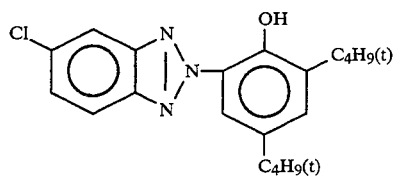
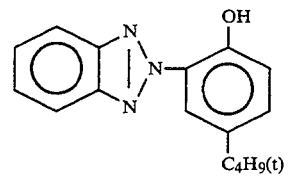

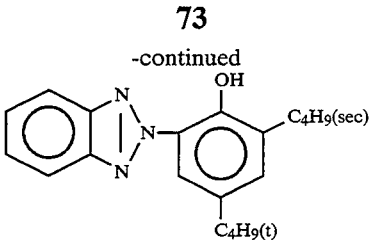

(Solv-1) Solvent:

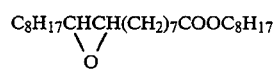

(Solv-2) Solvent:

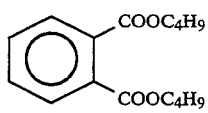

(Solv-3) Solvent:

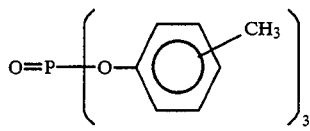

(Solv-4) Solvent:

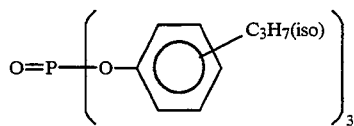

(Solv-5) Solvent:

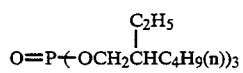

(Solv-6) Solvent:

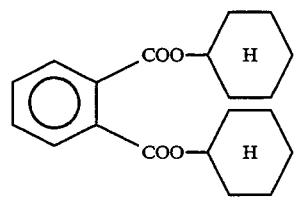

(Solv-7) Solvent:

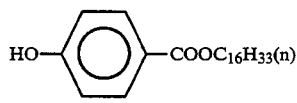

Photographic material Sample Nos. 302 to 311 were prepared in the same manner as in preparation of Sample No. 301, except that the cyan coupler (ExC-1) in Sample No. 301 was replaced by the same molar amount of coupler (I-7), (I-8), (I-12), (I-17), (I-21), (II-1), (II-4), (I-24), (II-30), (II-31), (II-35), (II-9), (II-11) and (II-14), respectively, of the present invention.

These Sample Nos. 301 to 315 each were subjected to gray exposure so that about 30% of the coated silver amount was developed, using a sensitometer (FWH Model, manufactured by Fuji Photo Film Co.; with a color temperature of the light source of being 3200° K.).

The exposed samples were processed by continuous processing with a paper processing machine, in accordance with the process mentioned below using the processing solutions also mentioned below, whereupon a developed condition of a running equilibrated condition was achieved.

Process:

| Processing Step | Temperature | Time | Amount of Replenisher (*) | Tank Capacity |
|---|---|---|---|---|
| Color Development | 35° C. | 45 sec | 161 ml | 17 liters |
| Bleach-fixation | 30 to 35° C. | 45 sec | 215 ml | 17 liters |
| Rinsing | 30° C. | 90 sec | 350 ml | 10 liters |
| Drying | 70 to 80° C. | 60 sec | | |

(*) per m2 of sample being processed.

The composition of the processing solutions used above is mentioned below.

| Color Developer | Tank Solution | Replenisher |
|---|---|---|
| Water | 800 ml | 800 ml |
| Ethylenediamine-N,N,N',N'-tetramethylenephosphonic Acid | 1.5 g | 2.0 g |
| Potassium Bromide | 0.015 g | |
| Triethanolamine | 8.0 g | 12.0 g |
| Sodium Chloride | 1.4 g | |
| Potassium Carbonate | 25 g | 25 g |
| N-ethyl-N-(β-methanesulfon-amidoethyl)-3-methyl-4-aminoaniline Sulfate | 5.0 g | 7.0 g |
| N,N-bis(carboxymethyl)hydrazine | 4.0 g | 5.0 g |
| N,N-di(sulfoethyl)hydroxylamine Monosodium Salt | 4.0 g | 5.0 g |
| Brightening Agent (WHITEX 4B, produced by Sumitomo Chemical Co.) | 1.0 g | 2.0 g |
| Water to make | 1000 ml | 1000 ml |
| pH (25° C.) | 10.05 | 10.45 |

| Bleach-Fixing Solution (tank solution and replenisher were same) | |
|---|---|
| Water | 400 ml |
| Ammonium Thiosulfate (700 g/liter) | 100 ml |
| Sodium Sulfite | 17 g |
| Ammonium Ethylenediaminetetraacetato/Iron(III) | 55 g |
| Disodium Ethylenediaminetetraacetate | 5 g |
| Ammonium Bromide | 40 g |
| Water to make | 1000 m |
| pH (25° C.) | 6.0 |

Rinsing Solution (tank solution and replenisher were same):

Ion-exchanged Water (having calcium and magnesium content of each being 3 ppm or less).

The processed Sample Nos. 302 to 315 were identified to have a better green reproducibility by side absorption at about 400 mm, than Sample No. 301.

The cyan reelection density of each of the processed samples was measured with a Fuji System Densitometer (F.S.D.). After being processed, the samples were stored under the conditions of 80° C. and 70% RH for one month, and the cyan reflection density of each was again measured. The variation of the density of each of the stored samples from the density of 1.5 of each of the corresponding fresh samples was obtained.

| Sample No. | Coupler | Color Fastness (Residual Dye) (%) |
|---|---|---|
| 301 | ExC-1 | 65 |
| 302 | (I-7) | 68 |
| 303 | (I-8) | 68 |
| 304 | (I-12) | 70 |
| 305 | (I-17) | 67 |
| 306 | (I-21) | 68 |
| 307 | (II-1) | 68 |
| 308 | (II-4) | 70 |
| 309 | (II-9) | 68 |
| 310 | (II-11) | 70 |
| 311 | (II-14) | 66 |
| 312 | (I-24) | 70 |
| 313 | (II-30) | 69 |
| 314 | (II-31) | 70 |
| 315 | (II-35) | 70 |

It was confirmed that all processed Sample Nos. 302 to 315 of the present invention yielded satisfactory dyes with a high coloring property and that they were free from reduction of the colored density even after storage.

EXAMPLE 4

Photographic material Sample No. 401 was prepared in the same manner as Sample No. 301 of Example 3, except for the following points:

An emulsified Dispersion A for the coating liquid for the first layer was prepared by dissolving 6.0 g of color image stabilizer (Cpd-1), 3.0 g of color image stabilizer (Cpd-2) and 6.0 g of color image stabilizer (Cpd-3) in 10 g of solvent (Solv-1), 10 g of solvent (Solv-2) and 100 cc of ethyl acetate, followed by emulsifying and dispersing the resulting solution in 500 g of an aqueous 10 gelatin solution containing 60 cc of 10% sodium dodecylbenzenesulfonate and 10 g of citric acid. An emulsified Dispersion C for the coating liquid for the fifth layer was prepared by adding 60.0 cc of ethyl acetate to 22.0 g of cyan coupler (ExC-1), 18.0 g of ultraviolet absorbent (UV-2), 20.0 g of color image stabilizer (Cpd-1), 12.0 g of color image stabilizer (Cpd-9), 12.0 g of color image stabilizer (Cpd-10), 1.0 g of color image stabilizer (Cpd-11), 1.0 g of color image stabilizer (Cpd-8), 1.0 g of color image stabilizer (Cpd-6), 15.0 g of solvent (Solv-6) and 1.0 g of solvent (Solv-1) and dissolving these various compounds in the ethyl acetate. The resulting solution was added to 500 cc of an aqueous 20% gelatin solution containing 8 cc of sodium dodecylbenzenesulfonate and thereafter it was emulsified and dispersed with an ultrasonic homogenizer. The layer constitution was varied so that the first layer contained 0.60 g/m$^2$ of yellow coupler (ExY), 0.06 g of color image stabilizer (Cpd-1), 0.03 g of color image stabilizer (Cpd-2), 0.06 g of color image stabilizer (Cpd-3), 0.10 g of solvent (Solv-1) ana 0.10 g of solvent (Solv-2); so that the second layer contained 0.07 g of color mixing preventing agent (Cpd-4); that the fourth layer contained 0.05 g of color mixing preventing agent (Cpd-4); so that the fifth layer contained 0.18 g of silver chloride Emulsion C, 0.22 g of cyan coupler (ExC-1), 0.20 g of color image stabilizer (Cpd-1), 0.12 g on color image stabilizer (Cpd-9), 0.12 g of color image stabilizer (Cpd-10) and 0.15 g of solvent (Solv-6); and the sixth layer contained 0.40 g of ultraviolet absorbent (UV-1). The other layers of Sample No. 401 were same as those of Sample No. 301.

Sample Nos. 402 to 413 were prepared in the same manner as in preparation of Sample No. 401, except that cyan coupler (ExC-1) was replaced by the same molar amount of the coupler shown in Table C below.

These Sample Nos. 401 to 413 were each subjected to gray exposure in order that about 30% of the coated silver amount was developed, using a sensitometer (FWH Model, manufactured by Fuji Photo Film Co.; with a color temperature of the light source of being 3200° K.).

The exposed samples were processed by continuous processing with a paper processing machine, in accordance with the same process as that in Example 3 using the same processing solutions as those in Example 3, whereupon a developed condition of a running equilibrated condition was achieved.

Next, each of the samples was subjected to three-color separation exposure, using a sensitometric optical wedge; and the exposed samples were then processed with the above-mentioned processing solutions under the above mentioned running equilibrated condition. The processed samples were subjected to sensitometric measurement. Visually observing the cyan color area of each of the processed samples, it was clear that Sample Nos. 403 to 413 each containing the coupler of the present invention, each yielded a more vivid cyan color having an obviously higher color density and having a higher transparency than the comparative Sample No. 401. The fog density (Dmin) and the maximum color density (Dmax) as read from the sensitometry curve are shown in Table C below.

TABLE C

| Sample No. | Coupler | Dmin | Dmax | Remarks |
|---|---|---|---|---|
| 401 | ExC-1 | 0.12 | 1.74 | comparative sample |
| 402 | ExC | 0.25 | 2.04 | comparative sample |
| 403 | (III-1) | 0.11 | 2.41 | sample of the invention |
| 404 | (III-3) | 0.11 | 2.39 | sample of the invention |
| 405 | (III-13) | 0.12 | 2.37 | sample of the invention |
| 406 | (III-14) | 0.12 | 2.28 | sample of the invention |
| 407 | (III-17) | 0.13 | 2.25 | sample of the invention |
| 408 | (III-2) | 0.11 | 2.19 | sample of the invention |
| 409 | (III-19) | 0.12 | 2.08 | sample of the invention |
| 410 | (I-24) | 0.10 | 2.10 | sample of the invention |
| 411 | (II-30) | 0.11 | 1.95 | sample of the invention |
| 412 | (II-31) | 0.12 | 1.93 | sample of the invention |
| 413 | (II-35) | 0.12 | 1.95 | sample of the invention |

From Table C above, it is noted that Sample No. 402 containing a known coupler ExC which is known to yield a dye having an excellent color hue, had a higher coloring property than the comparative coupler ExC-1 in Sample No. 401 but the former gave a noticeable fog. On the other hand, Sample Nos. 403 to 413 each containing the coupler of the present invention, had a much higher coloring property than the coupler in Sample No. 402 and gave a lower fog than the same. Thus, it is evident that the couplers of the present invention are excellent with respect to the color hue of the dye formed therefrom and the coloring property, and because they cause little fog.

Next, other samples were prepared in the same manner as in preparation of Sample Nos. 401 to 413 of Example 4, except that the yellow coupler (ExY) in the first layer (blue-sensitive emulsion layer) was replaced by the same molar amount of ExY-2 and except that the amount of the first layer to be coated, including the coupler, was reduced to 80% without changing the other components therein. These samples were evaluated in the same manner as in Example 4. Almost the same results were obtained for these samples.

(ExY-2):

fourth layers of Sample No. 701 was replaced by the couplers identified in the first full paragraph of pages 113 and Table C, shown in the previous Examples 3 and 4. These samples were evaluated in the same manner as in Examples 3 and 4. Almost the same results were obtained for these samples.

Next, other samples were prepared in the same manner as above, except that 0.050 g/m² of Ex-14 was added to the fourth layer, 0,020 g/m² of Ex-15 was added to the fifth layer, and 0.015 g/m² of Ex-2 was added to the ninth layer, and additionally Ex-11 and Ex-13 in the ninth layer were replaced by 0.065 g/m² of Ex-16 and 0.020 g/m² of Ex-17, respectively. These samples were evaluated in the same manner as in Examples 3 and 4. Almost the same results were obtained for these samples.

Still other samples were prepared in the same manner as above, except that Ex-8 and Ex-9 in the eleventh,

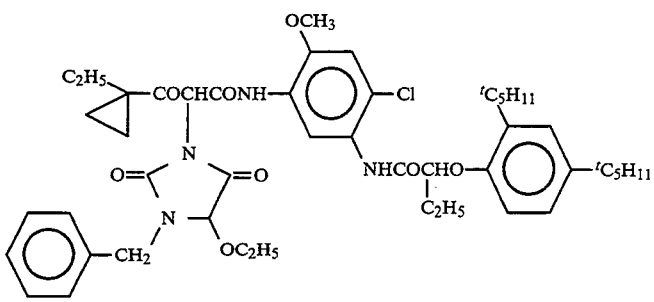

EXAMPLE 5

A sample having the same constitution as Sample No. 701 of Example 7 of JP-A 2-139544 was prepared. Next, other samples were prepared in the same manner, except that the cyan coupler (Ex-2) in the third and twelfth and thirteenth layers were replaced by the same molar amounts of Ex-18 and Ex-19, respectively. These samples were evaluated in the same manner as in Examples 3 and 4. Almost the same results were obtained for these samples.

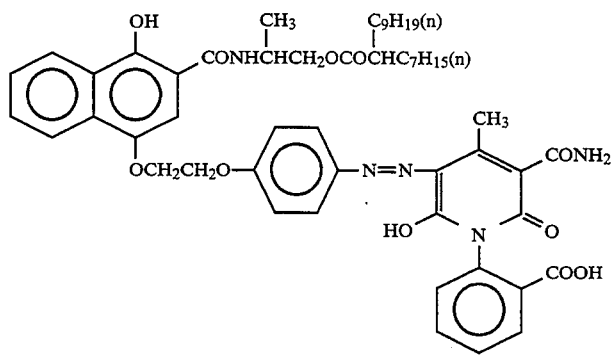

Ex-14

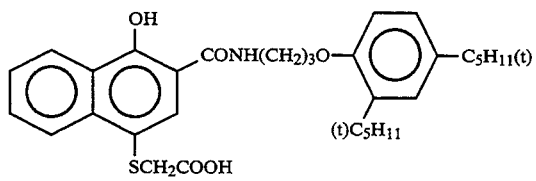

Ex-15

-continued

Ex-16
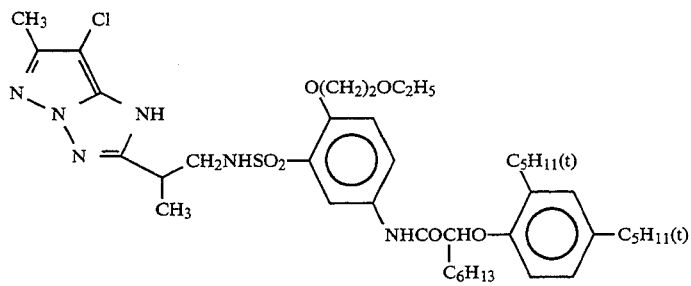

Ex-17
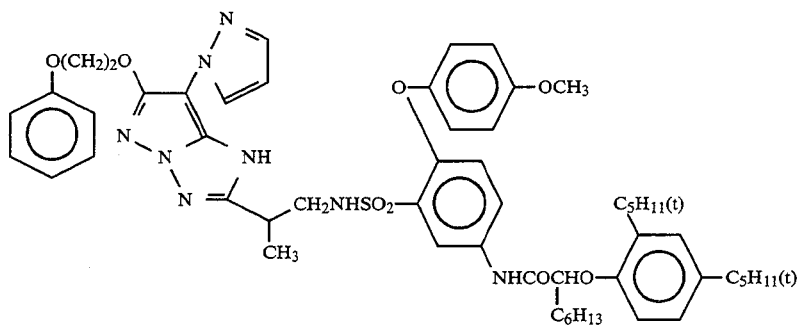

Ex-18
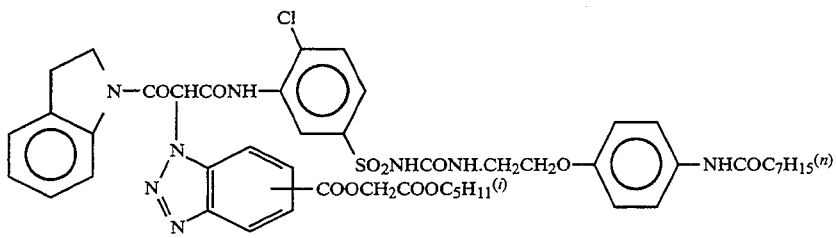

Ex-19
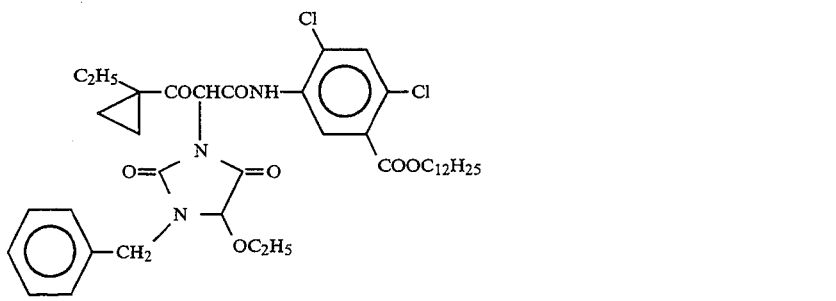

EXAMPLE 6

A sample having the same constitution as Sample No. 601 of Example 6 of JP-A 2-13944 was prepared. Next, other samples were prepared in the same manner, except that the cyan couplers C-1, C-2 and C-3 in the fourth, fifth and sixth layers of Sample No. 601 were replaced by the couplers identified in the first paragraph of page 113 and Table C shown in the previous Examples 3 and 4. These samples were evaluated in the same manner as in Examples 3 and 4. Almost the same results were obtained for these samples.

Next, still other samples were prepared in the same manner as above, except that C-6 in the sixteenth and seventeenth layers was replaced by the same molar amount of C-10 and that C-4 and C-7 in the ninth to eleventh layers were replaced by 80 mol % of C-8. These samples were evaluated in the same manner as in Examples 3 and 4. Almost the same results were obtained for these samples.

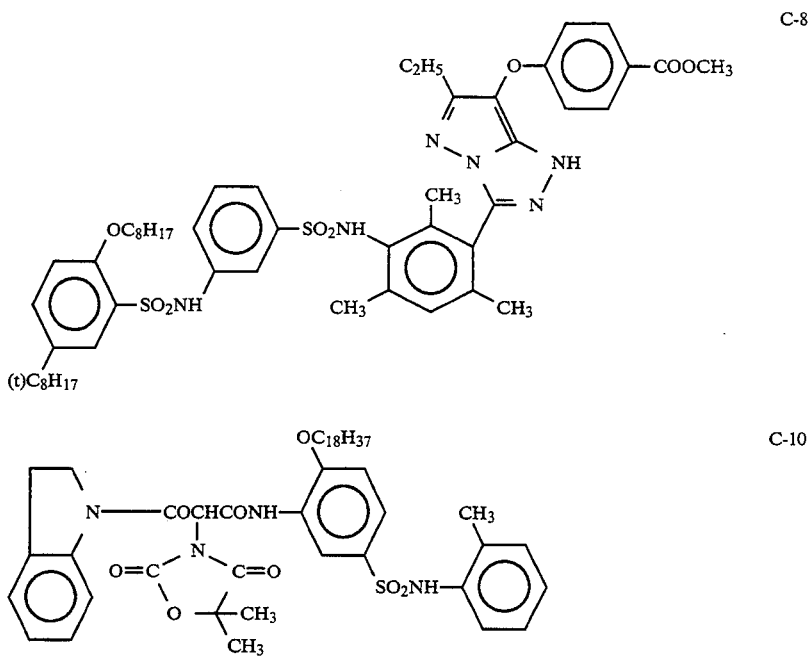

C-8

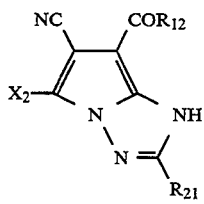

C-10

As explained in detail in the above, the present invention provides an excellent silver halide photographic material for forming a color image having an excellent color hue, a high color fastness, and a reduced fog.

While the invention has been described in detail and with reference to specific embodiments thereof, it will be apparent to one skilled in the art that various changes and modifications can be made therein without departing from the spirit and scope thereof.

What is claimed is:

1. A silver halide color photographic material, comprising a support having thereon at least one red-sensitive silver halide emulsion layer containing at least one cyan coupler of the following general formula (I):

(I)

wherein $R_{11}$ represents a branched or cyclic alkyl group, a branched or cyclic alkoxy group, a substituted aryl group, or a substituted aryloxy group;

$R_{21}$ represents a substituent;

$X_1$ represents a hydrogen atom or a group which is capable of splitting off from the formula by a coupling reaction with an oxidation product of an aromatic primary amine color developing agent; and a group represented by $R_{11}$, $R_{21}$ or $X_1$ may be divalent and form a dimer or a higher polymer or bond to a polymer chain to form a homopolymer of copolymer.

2. The silver halide color photographic material as claimed in claim 1, wherein the substituted aryl group in $R_{11}$ formula (I) is represented by formula (IV) and the substituted aryloxy group in $R_{11}$ of formula (I) is represented by formula (V);

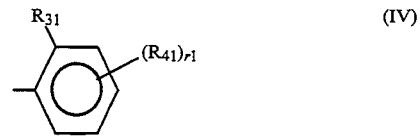

(IV)

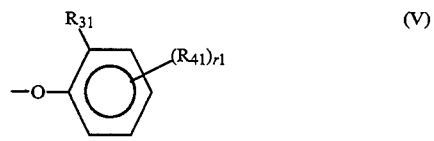

(V)

wherein $R_{31}$ and $R_{41}$ may be same or different and each represents a substituent; and $r_1$ represents an integer of from 0 to 4, and when $r_1$ is a plural number, the plurality of $R_{41}$ groups may be the same or different.

3. The silver halide color photographic material as claimed in claim 2, wherein $R_{31}$ and $R_{41}$ each represents a halogen atom, an aliphatic group, an aryl group, a heterocyclic group, an alkoxy group, an aryloxy group, a heterocyclic oxy group, a heterocyclic thio group, an acyloxy group, a silyloxy group, an alkyl- or arylsulfamoyloxy group, an acylamino group, an alkylamino group, an arylamino group, a ureido group, a sulfamoylamino group, an alkenyloxy group, a formyl group, an alkyl-, aryl- or heterocyclic acyl group, an alkyl-, aryl-, or heterocyclic sulfonyl group, a sulfinyl group, an alkyl-, aryl- or heterocyclic oxycarbonyl group, an alkyl-, aryl- or heterocyclic oxycarbonylamino group, a sulfonamido group, a carbamoyl group, a sulfamoyl group, a phosphonyl group, an imido group, an azolyl group, a hydroxyl group, a cyano group, a carboxyl group, a nitro group, a sulfo group, or an unsubstituted amino group.

4. The silver halide color photographic material as claimed in claim 1, wherein $R_{11}$ in formula (I) represents a branched or cyclic alkoxy group or a substituted aryloxy group.

5. The silver halide color photographic material as claimed in claim 4, wherein $R_{11}$ represents a branched or cyclic alkoxy group.

6. The silver halide color photographic material as claimed in claim 4, wherein $R_{11}$ represents a branched alkoxy group.

7. The silver halide color photographic material as claimed in claim 1, wherein $R_{21}$ represents a halogen atom, an alkyl group, an aryl group, a heterocyclic group, an alkoxy group, an aryloxy group, a heterocyclic oxy group, an acyloxy group, an acylamino group, an alkylamino group, an anilino group, a ureido group, a sulfamoylamino group, an alkenyloxy group, an alkyl-, aryl- or heterocyclic acyl group, an alkyl-, aryl-, or heterocyclic sulfonyl group, a sulfinyl group, an alkyl-, aryl- or heterocyclic oxycarbonyl group, an alkyl-, aryl- or heterocyclic oxycarbonylamino group, a sulfonamido group, a carbamoyl group, a sulfamoyl group, an imido group, a hydroxyl group, a cyano group, a carboxyl group, a nitro group, or a sulfo group.

8. The silver halide color photographic material as claimed in claim 7, wherein $R_{21}$ represents an alkyl group, an aryl group, a carbamoyl group, an acylamino group, or a ureido group.

9. The silver halide color photographic material as claimed in claim 8, wherein $R_{21}$ represents an aryl group.

10. The silver halide color photographic material as claimed in claim 1, wherein $X_1$ represents a hydrogen atom, a halogen atom, an alkoxy group, an aryloxy group, an acyloxy group, an alkyl- or arylsulfonyloxy group, an acylamino group, an alkyl- or arylsulfonamido group, an alkoxycaronyloxy group, an aryloxycaronyloxy group, an alkyl-, aryl- or heterocyclic thio group, a carbamoylamino group, a 5- or 6-membered heterocyclic group, an imido group, or an arylazo group.

11. The silver halide color photographic material as claimed in claim 1, wherein the cyan coupler of formula (I) is contained in an amount of from $1 \times 10^{-3}$ mol to 1 mol/mol of silver halide.

12. A silver halide color photographic material, comprising a support having thereon at least one red-sensitive silver halide emulsion layer containing at least one cyan coupler of the following general formula (II):

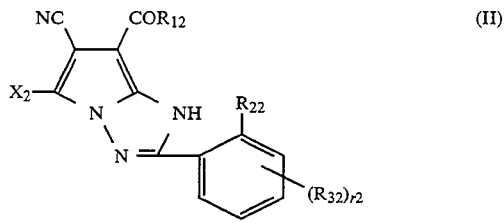

wherein $R_{12}$ represents an aliphatic group, an aryl group, a heterocyclic group, an alkoxy group, an aryloxy group, an alkylamino group, an anilino group, a heterocyclic oxy group, or a heterocyclic amino group;
$R_{22}$ and $R_{32}$ each represents a substituent;
$r_2$ represent an integer of from 0 to 4; provided that when $r_2$ is a plural number, the plurality of $R_{32}$ groups may be the same or different;
$X_2$ represents a hydrogen atom or a group which is capable of splitting off from the formula by a coupling reaction with an oxidation product of an aromatic primary amine color developing agent; and a group represented by $R_{12}$, $R_{22}$, $R_{32}$ or $X_2$, may be divalent and form a dimer or a higher polymer or bond to a polymer chain to form a homopolymer of copolymer.

13. The silver halide color photographic material as claimed in claim 12, wherein $R_{22}$ and $R_{32}$ each represents a halogen atom, an alkyl group, an aryl group, a heterocyclic group, an alkoxy group, an aryloxy group, a heterocyclic oxy group, a heterocyclic thio group, an acyloxy group, a silyloxy group, an acylamino group, an alkylamino group, an anilino group, a ureido group, a sulfamoylamino group, a sulfinyl group, an alkyl- or aryl oxycarbonyl group, an alkyl- or aryl- oxycarbonylamino group, a sulfonamido group, a carbamoyl group, a sulfamoyl group, a phosphonyl group, an imido group, an azolyl group, a hydroxyl group, a cyano group, a carboxyl group, a nitro group, or a sulfo group.

14. The silver halide color photographic material as claimed in claim 12, wherein $R_{12}$ represents an alkoxy group, an aryloxy group, an alkylamino group, or an anilino group.

15. The silver halide color photographic material as claimed in claim 14, wherein $R_{12}$ represents a branched or cyclic alkoxy group or a substituted aryloxy group.

16. The silver halide color photographic material as claimed in claim 12, wherein $R_{22}$ represents an alkyl group, an alkoxy group, an acylamino group, a sulfonamido group, a halogen atom, a ureido group, an alkylamino group, an anilino group or a carbamoyl group.

17. The silver halide color photographic material as claimed in claim 12, wherein $X_2$ represents a hydrogen atom, a halogen atom, an alkoxy group, an aryloxy group, an acyloxy group, an alkyl- or arylsulfonyloxy group, an acylamino group, an alkyl- or arylsulfonamido group, an alkoxycarbonyloxy group, an aryloxycarbonyloxy group, an alkyl-, aryl- or heterocyclic thio group, a carbamoylamino group, a 5- or 6-membered heterocyclic group, an imido group, or an arylazo group.

18. The silver halide color photographic material as claimed in claim 12, wherein the cyan coupler of formula (II) is contained in an amount of from $1 \times 10^{-3}$ mol to 1 mol/mol of silver halide.

* * * * *